(12) United States Patent
Ihara

(10) Patent No.: US 7,693,683 B2
(45) Date of Patent: Apr. 6, 2010

(54) INFORMATION CLASSIFYING DEVICE, INFORMATION CLASSIFYING METHOD, INFORMATION CLASSIFYING PROGRAM, INFORMATION CLASSIFYING SYSTEM

(75) Inventor: Masayoshi Ihara, Saitama (JP)

(73) Assignee: Sharp Kabushiki Kaisha, Osaka (JP)

(*) Notice: Subject to any disclaimer, the term of this patent is extended or adjusted under 35 U.S.C. 154(b) by 349 days.

(21) Appl. No.: 11/791,705

(22) PCT Filed: Nov. 17, 2005

(86) PCT No.: PCT/JP2005/021095

§ 371 (c)(1),
(2), (4) Date: May 25, 2007

(87) PCT Pub. No.: WO2006/087854

PCT Pub. Date: Aug. 24, 2006

(65) Prior Publication Data

US 2008/0114564 A1 May 15, 2008

(30) Foreign Application Priority Data

| Nov. 25, 2004 | (JP) | ............................. 2004-340723 |
| May 19, 2005 | (JP) | ............................. 2005-147048 |

(51) Int. Cl.
G06F 17/18 (2006.01)
G06F 17/30 (2006.01)
G06K 9/62 (2006.01)

(52) U.S. Cl. ................. 702/179; 382/224; 707/E17.089

(58) Field of Classification Search ................. 702/179, 702/158, 181, 155, 182; 703/2; 704/231, 704/234, 238–240, 243, 245; 382/106, 181, 382/224, 225; 707/1–10, 101, E17.089
See application file for complete search history.

(56) References Cited

U.S. PATENT DOCUMENTS 6,442,555 B1 * 8/2002 Shmueli et al. ............. 707/101

(Continued)

FOREIGN PATENT DOCUMENTS

JP 9-161062 A 6/1997

(Continued)

OTHER PUBLICATIONS

Yoshihiko Hamamoto, The Institute of Electronics, Information and Communication Engineers Gijutsu Kenkyu Holoku, vol. 100, No. 507, Dec. 7, 2000.

(Continued)

Primary Examiner—Michael P. Nghiem
Assistant Examiner—Toan M Le
(74) Attorney, Agent, or Firm—Birch, Stewart, Kolasch & Birch, LLP

(57) ABSTRACT

An information classifying device calculates, for a plurality of populations containing pieces of sample information, evaluation distance between a center of gravity of the pieces of sample information belonging to each population and a piece of sample information as an object of classification (object sample), calculates statistical information such as mean, variance and standard deviation of the evaluation distance for each population, evaluates the evaluation distance of the sample information to the population based on the evaluation distance and the statistical information and evaluates degree of assignment relevancy of the object sample to the population, determines to which population the object sample is to be assigned in accordance with the degree of assignment relevancy, and assigns the object sample to the population. Evaluation distance between the center of gravity of each updated population and the object sample belonging to each population is calculated. If the degree of assignment relevancy to every population is out of a prescribed range, a new population is formed, and the object sample is assigned to the new population. Thus, autonomous and stable classification of object sample to a population becomes possible.

28 Claims, 6 Drawing Sheets

U.S. PATENT DOCUMENTS

| | | | |
|---|---|---|---|
| 6,704,905 B2 | 3/2004 | Fukushige et al. | |
| 6,728,658 B1 * | 4/2004 | Bechhoefer | 702/181 |
| 7,117,108 B2 * | 10/2006 | Rapp et al. | 702/71 |
| 7,548,651 B2 * | 6/2009 | Shozakai et al. | 382/224 |
| 2003/0018629 A1 | 1/2003 | Namba | |

FOREIGN PATENT DOCUMENTS

| | | |
|---|---|---|
| JP | 2001-167124 A | 6/2001 |
| JP | 2002-183171 A | 6/2002 |
| JP | 2002183171 A * | 6/2002 |
| JP | 2002-202983 A | 7/2002 |
| JP | 2003-30224 A | 1/2003 |
| JP | 2003-76976 A | 3/2003 |

OTHER PUBLICATIONS

Fukashi Kojyo et al., material of Technical Society of Measurement, Institute of Electrical Engineers of Japan, Oct. 2003, IM-03-55, pp. 13-18.

Koji Iwano et al., paper of 2005 Spring Meeting of The Acoustical Society of Japan, Mar. 2005, vol. 1, 2-1-14, pp. 231-232.

* cited by examiner (A) CLASSIFICATION BEFORE PROCESSING

○ : aₙ   ◇ : bₘ   ★ : EACH CENTER OF GRAVITY
—————— BOUNDARY OF MANUAL CLASSIFICATION
—·—·— 3σ BOUNDARY OF POPULATION A
—··—  3σ BOUNDARY OF POPULATION B (B) CLASSIFICATION AFTER PROCESSING
BY THE PRESENT METHOD

○ : aₙ   ◇ : bₘ   ★ : EACH CENTER OF GRAVITY
— — — NEW CLASSIFICATION BOUNDARY

US 7,693,683 B2

INFORMATION CLASSIFYING DEVICE, INFORMATION CLASSIFYING METHOD, INFORMATION CLASSIFYING PROGRAM, INFORMATION CLASSIFYING SYSTEM

TECHNICAL FIELD

The present invention relates to an information classifying device, an information recognizing device, an information searching device, an information classifying method, an information classifying program, an information classifying system, an information providing service using the information classifying system, a computer-readable recording medium recording a classified population classified by the information classifying system, and to a database storing an arbitrary number of populations allowing a search for a population to which sample information as an object of classification belongs, using the information classifying system. Particularly, the present invention relates to an information classifying device, an information recognizing device, an information searching device, an information classifying method, an information classifying program, an information classifying system, an information providing service using the information classifying system, a computer-readable recording medium recording a classified population classified by the information classifying system, and to a database storing an arbitrary number of populations allowing a search for a population to which sample information as an object of classification belongs, using the information classifying system, that are suitable for statistically classifying information.

BACKGROUND ART

As methods of classifying or recognizing pieces of information, generally, a method in which matrix information groups are subjected to orthogonal decomposition to find an optimal solution using a plurality of matrix information groups, Baum-Welch algorithm as a method of likelihood estimation, or an algorithm for mathematically calculating an optimal solution such as minimum error classification, has been used.

Further, a method has been known in which a neural network is corrected such that Mahalanobis distance is maintained at an arbitrary, constant distance, when an optimal value of an intermediate layer in the neural network is to be calculated (see, for example, Japanese Patent Laying-Open No. 2003-76976 (hereinafter referred to as "Patent Document 1")).

As a method of vector quantization, a method referred to as K-means has been known, in which an arbitrary center of gravity is applied to a population and recursive classification is continued until the center of gravity reaches an optimal position.

Patent Document 1 discloses a method of optimizing boundary conditions by maintaining Mahalanobis distance constant.

Further, as a method of dividing mixture distribution, expectation maximization, referred to as EM algorithm, has been known in which local solutions are continuously changed to find a local optimal solution in inductive manner, based on frequency distribution of sample appearance and likelihood distribution.

As another method of dividing mixture distribution, a method referred to as support vector machine has been known. According to this method, a non-linear map of a population is transformed to a space of different dimension using an arbitrary function, to determine boundary condition and boundary width.

According to an article "An Estimation of Data Distribution with a Neural Network Model Based on Bayesian Estimation", Fukashi KOJYO and Hiroshi WAKUYA, material of Technical Society of Measurement, Institute of Electrical Engineers of Japan, October 2003, IM-03-55, pp. 13-18 (hereinafter referred to as Non-Patent Document 1), evaluation for estimating mean and variance as well as standard deviation of a population is performed in accordance with Bayes method, by evaluating whether each sample position is within a specific range of standard deviation or not from the center of gravity of the entire population. Further, "Analysis of Cepstral Features of Japanese Spontaneous Speech Using Mahalanobis Distance", Masanobu NAKAMURA, Koji IWANO and Sadaoki FURUI, paper of 2005 Spring Meeting of The Acoustical Society of Japan, March 2005, vol. 1, 2-1-14, pp. 231-232 (hereinafter referred to as Non-Patent Document 2) describes high accuracy of phoneme evaluation using Mahalanobis distance.

Methods involving division of mixture distribution and vector quantization as described above have been generally used.

Patent Document 1: Japanese Patent Laying-Open No. 2003-76976

Non-Patent Document 1: "An Estimation of Data Distribution with a Neural Network Model Based on Bayesian Estimation", Fukashi KOJYO and Hiroshi WAKUYA, material of Technical Society of Measurement, Institute of Electrical Engineers of Japan, October 2003, IM-03-55, pp. 13-18.

Non-Patent Document 2: "Analysis of Cepstral Features of Japanese Spontaneous Speech Using Mahalanobis Distance", Masanobu NAKAMURA, Koji IWANO and Sadaoki FURUI, paper of 2005 Spring Meeting of The Acoustical Society of Japan, March 2005, vol. 1, 2-1-14, pp. 231-232.

DISCLOSURE OF THE INVENTION

Problems to be Solved by the Invention

FIG. 7 shows an example of normal distribution. FIG. 8 shows an example of non-normal distribution. Generally, in the background technology described above, boundary of a population designated by a person inevitably becomes vague dependent on the condition of human interpretation of information, and therefore, a non-normal distribution referred to as the mixture distribution such as shown in FIG. 8 is formed. This poses a problem that population boundary cannot be arithmetically obtained from optimal solution based on the premise of normal distribution such as shown in FIG. 7.

In addition, as the mixture distribution is not always a mixed normal distribution, a number of local solutions of high likelihood appear, each can be interpreted as the optimal solution of normal distribution. As a result, too many or infinite number of optimal solutions as arithmetic solutions are generated, so that the optimal solutions lose practical meaning and, in addition, the number of populations for classification increases indefinitely, leading to a general problem that stable classification to the populations is not always possible.

According to K-means method, when the arbitrary center of gravity identified at the initial stage is inappropriate, the number of initial populations will be the number of populations after optimization, which means that autonomous increase/decrease of the populations does not take place, and hence, there is a problem that stable classification to the populations is not always possible.

Patent Document 1 simply describes that the neural network functions optimally when Mahalanobis distance is kept constant. Therefore, even when application to clustering is assumed, classification would be into the inside and outside of the mean distance value of samples forming the population, and hence, the problem that the number of populations increases to be larger than necessary or infinitely cannot be solved.

It has been known that EM algorithm provides local solutions infinitely or more than necessary, leading to the problem that stable classification to the populations is not always possible.

Further, SVM is a method of determining boundary condition and boundary width by transforming a non-linear map of a population to a space of different dimension, using an arbitrary function, and SVM has the problem that stable classification to the populations is not always possible.

Further, the method of estimating data distribution based on Bayseian inference according to Non-Patent Document 1 relates to evaluation of belonging, based on variation and standard deviation with the center of gravity of the population being the mean, and evaluates an output layer of a multi-layered neural network. Different from the present invention, it does not present any problem related to information classification or prove solution of the problem, through evaluation of sample distance using mean of evaluation distances and standard deviation thereof in the population to which the samples belong.

Non-Patent Document 2 provides results of analysis and consideration that speech analysis utilizing Mahalanobis distance has high correlation, and this article does not present any specific problem, solution to the problem or proof.

Further, in such information classification systems, there is a problem that evaluation functions of vectors and/or matrixes and/or tensors having different items and orders of feature elements cannot be evaluated with each other.

The present invention was made to solve the above-described problems, and one of the objects of the present invention is to provide an information classifying device, an information recognizing device, an information searching device, an information classifying method, an information classifying program and an information classifying system, that allow autonomous and stable classification of pieces of sample information to populations.

Another object of the present invention is to provide an information classifying device, an information recognizing device, an information searching device, an information classifying method, an information classifying program and an information classifying system, that allow mutual evaluation of pieces of sample information having different elements configurations.

Means for Solving the Problems

In order to solve the above-described problem, according to an aspect, the present invention provides an information classifying device including a distance calculating unit, a statistical information calculating unit, a degree of assignment relevancy evaluating unit, an assignment destination determining unit, and a sample information classifying unit.

The distance calculating unit calculates distance information between each of an arbitrary number of pieces of sample information and center of gravity of each of an arbitrary number of populations including pieces of sample information, using a distance evaluation function. The statistical information calculating unit calculates statistical information using mean of sample distances and variance of sample distances with the mean of sample distances being the center, based on each group of distance information constituted by the distance information calculated by the distance calculating unit, associated with each sample information belonging to each population.

The degree of assignment relevancy evaluating unit evaluates degree of assignment relevancy by calculating distance between the center of gravity of each population and sample information as an object of classification using the distance calculating unit, normalizing the distance using the statistical information calculated by the distance calculating unit on the calculated distance and performing a statistical test. The assignment destination determining unit determines to which population the piece of information as the object of classification is to be assigned, in accordance with the degree of assignment relevancy determined by the degree of assignment relevancy determining unit. The sample information classifying unit assigns and classifies the piece of sample information as the object of classification to the population determined by the assignment destination determining unit.

According to the present invention, by the information classifying device, distance information between each of an arbitrary number of pieces of sample information and center of gravity of each of an arbitrary number of populations including pieces of sample information is calculated using a distance evaluation function, statistical information is calculated using mean of sample distances and variance of sample distances with the mean of sample distances being the center, based on each group of distance information constituted by the calculated distance information, associated with each sample information belonging to each population, distance between the center of gravity of each population and sample information as an object of classification is calculated, degree of assignment relevancy is evaluated, by normalizing the distance using the calculated statistical information on the calculated distance and performing a statistical test, to which population the piece of information as the object of classification is to be assigned is determined in accordance with the evaluated degree of assignment relevancy, and the piece of sample information as the object of classification is assigned and classified to the determined population.

Therefore, by the information classifying device, the piece of sample information as the object of classification is assigned and classified to any of the populations, in accordance with the degree of assignment relevancy to the population. As a result, an information classifying device allowing autonomous and stable classification of pieces of sample information to populations can be provided.

Preferably, the statistical information is statistical information formed by further adding standard deviation (S13) of sample distance based on each group of the distance information belonging to each population, and the assignment relevancy evaluating unit evaluates degree of assignment relevancy of the sample information as the object of classification to each population, dependent on a probability of assignment to each population, obtained by calculating distance between the center of gravity of each population and the sample information as the object of classification using the distance evaluation function by the distance calculating unit, and normalizing (S14) the distance to each sample information as the object of classification with the standard deviation using the calculated distance and the statistical information calculated by the statistical information calculating unit.

Preferably, the distance calculating unit further includes distance evaluation function reconfiguring unit for reconfiguring, after the sample information classifying unit forms updated populations having sample information groups updated based on the sample information as the object of classification, the distance evaluation function to be used by the distance calculating unit, in accordance with classified group of sample information for each updated population thus formed, and the distance calculating unit further calculates a group of distance information between the sample information as the object of classification belonging to each updated population and the center of gravity of the updated population, using the distance evaluation function reconfigured by the distance evaluation function reconfiguring unit.

According to the present invention, by the information classifying device, updated populations having sample information groups updated based on the sample information as the object of classification are formed, the distance evaluation function is reconfigured in accordance with the sample information group classified for each updated population thus formed, a group of distance information between the sample information as the object of classification belonging to each updated population and the center of gravity of the updated population is further calculated, using the reconfigured distance evaluation function, and based on the calculated distance information group, the piece of sample information as the object of classification is assigned and classified to any of the populations in accordance with the degree of assignment relevancy.

Therefore, it is possible by the information classifying device to further classify the piece of sample information to the population in a recursive manner.

Preferably, the assignment destination determining unit includes a population generating unit for generating a new population when degree of assignment relevancy to every population is out of a prescribed range, and determines that the piece of sample information as the object of classification should be assigned to the generated population.

According to the present invention, by the information classifying device, a new population is generated when the degree of assignment relevancy to every population is out of a prescribed range, and the piece of sample information as the object of classification is assigned and classified to the generated population.

Therefore, any piece of sample information belonging to a population has its degree of assignment relevancy within a prescribed range. As a result, it becomes possible by the information classifying device to classify the pieces of sample information to populations with the degree being within the prescribed range.

More preferably, the degree of assignment relevancy is deviation from the mean of distance information group for the population, and the prescribed degree is in a range in which the deviation is from the mean to a prescribed multiple of standard deviation.

According to the present invention, by the information classifying device, a new population is generated when the deviation from the mean value of distance information group to every population is out of the range of a prescribed multiple of standard deviation, and the piece of sample information as the object of classification is assigned to the generated population.

Therefore, by the information classifying device, it is possible to classify the piece of sample information with the deviation from the mean value of distance information group for the population being within the range of a prescribed multiple of standard deviation. As a result, it becomes possible to classify pieces of sample information to populations to attain near normal distribution in which pieces of sample information of a prescribed ratio belonging to a population are distributed in the range of prescribed multiple of standard deviation from the mean value.

More preferably, the information classifying device further includes a population removing unit for removing a population that does not contain at least a prescribed number of pieces of sample information, and for assigning pieces of sample information that belonged to the removed population to another population.

According to the present invention, by the information classifying device, a population not containing at least a prescribed number of pieces of sample information belonging thereto is removed, and the pieces of sample information that belonged to the removed population are assigned to a different population. Therefore, irrelevant population is culled out.

Preferably, the assignment destination determining unit determines that the piece of sample information as the object of classification is assigned to a population to which degree of assignment relevancy evaluated by the degree of assignment relevancy evaluating unit is the highest.

According to the present invention, the information classifying device determines that the piece of sample information as the object of classification should be assigned to the population having the best evaluated degree of assignment relevancy, and the piece of sample information as the object of classification is assigned to the determined population.

Therefore, by the information classifying device, the piece of sample information is assigned to the population to which degree of assignment relevancy is the highest. Therefore, optimal classification of sample information to the population becomes possible.

Preferably, the distance calculating unit calculates the distance information based on covariance structure analysis.

Preferably, the distance calculating unit calculates the distance information based on an eigen value and an eigen vector.

Preferably, the distance calculating unit calculates Mahalanobis distance as the distance information.

Preferably the distance calculating unit calculates distance in accordance with Bayesian discrimination function as the distance information.

Preferably, the distance calculating unit includes distance normalizing unit for normalizing the calculated distance information.

According to the present invention, the distance information is normalized by the information classifying device. As a result, the information classifying device allows easy handling of the distance information.

According to another aspect, the present invention provides an information recognizing device, including the information classifying device, and a recognizing unit for performing a process of recognizing identification information corresponding to a feature extracted from natural information using the distance evaluation function reconfigured by the distance evaluation function reconfiguring unit.

According to a still further aspect, the present invention provides an information searching device, including the information classifying device, a recognizing unit for performing a process of recognizing identification information corresponding to a feature extracted from natural information using the distance evaluation function reconfigured by the distance evaluation function reconfiguring unit, and a searching unit for performing a search, using result of recognition by the recognizing unit.

According to a further aspect, the present invention provides an information classification method executed by a computer, including the steps of: calculating distance information between each of an arbitrary number of pieces of sample information and center of gravity of each of an arbitrary number of populations including the pieces of sample information, using a distance evaluation function; calculating statistical information using mean of sample distances and variance of sample distances with the mean of sample distances being the center, based on each group of distance information constituted by the calculated distance information, associated with each sample information belonging to each population; evaluating degree of assignment relevancy by calculating distance between the center of gravity of each population and sample information as an object of classification and normalizing the distance using the calculated statistical information on the calculated distance and performing a statistical test; determining to which population the piece of information as the object of classification is to be assigned, in accordance with the evaluated degree of assignment relevancy; and assigning and classifying the piece of sample information as the object of classification to the determined population.

According to the present invention, an information classifying method that allows autonomous and stable classification of pieces of sample information to populations can be provided.

According to a still another aspect, the present invention provides an information classifying program executed by a computer, causing the computer to execute the steps of: calculating distance information between each of an arbitrary number of pieces of sample information and center of gravity of each of an arbitrary number of populations including the pieces of sample information, using a distance evaluation function; calculating statistical information using mean of sample distances and variance of sample distances with the mean of sample distances being the center, based on each group of distance information constituted by the calculated distance information, associated with each sample information belonging to each population; evaluating degree of assignment relevancy by calculating distance between the center of gravity of each population and sample information as an object of classification and normalizing the distance using the calculated statistical information on the calculated distance and performing a statistical test; determining to which population the piece of information as the object of classification is to be assigned, in accordance with the evaluated degree of assignment relevancy; and assigning and classifying the piece of sample information as the object of classification to the determined population.

According to the present invention, an information classifying program that allows autonomous and stable classification of pieces of sample information to populations can be provided.

According to a still further aspect, the present invention provides an information classifying system, including an information processing device, and an information terminal connected to the information classifying device through a communication line. The information classifying device includes a population receiving unit, a distance calculating unit, a statistical information calculating unit, a degree of assignment relevancy evaluating unit, an assignment destination determining unit, a sample information classifying unit, and a classified population passing unit. The information terminal includes a population passing unit and a classified population receiving unit.

The population passing unit passes an arbitrary number of populations containing pieces of sample information, to the information classifying device. The population receiving unit receives an arbitrary number of populations containing the pieces of sample information, from the information terminal. The distance calculating unit calculates distance information between each of an arbitrary number of pieces of sample information included in the populations received by the population receiving unit and center of gravity of each of the arbitrary number of populations, using a distance evaluation function.

The statistical information calculating unit calculates statistical information using mean of sample distances and variance of sample distances with the mean of sample distances being the center, based on each group of distance information constituted by the distance information calculated by the distance calculating unit, associated with each sample information belonging to each population. The degree of assignment relevancy evaluating unit evaluates degree of assignment relevancy by calculating distance between the center of gravity of each population and sample information as an object of classification using the distance calculating unit, and normalizing the distance using the statistical information calculated by the statistical information calculating unit on the calculated distance and performing a statistical test.

The assignment destination determining unit determines to which population the piece of information as the object of classification is to be assigned, in accordance with the degree of assignment relevancy determined by the degree of assignment relevancy determining unit. The sample information classifying unit assigns and classifies the piece of sample information as the object of classification to the population determined by the assignment destination determining unit.

The classified population passing unit passes a classified population, to which the piece of sample information as the object of classification has been assigned and classified by the sample information classifying unit, to the information terminal. The classified population receiving unit receives the classified population from the information classifying device.

According to the present invention, an information classifying system is obtained which can provide populations in which pieces of sample information are classified in autonomous and stable manner.

According to a still further aspect, the present invention provides an information classifying system including an information classifying device, and an information terminal connected to the information classifying device through a communication line. The information classifying device includes a sample information receiving unit, a distance calculating unit, a statistical information calculating unit, a degree of assignment relevancy evaluating unit, an assignment destination determining unit, and a population identifying information passing unit. The information terminal includes a sample information passing unit and a population identifying information receiving unit.

The sample information passing unit passes the sample information as the object of classification to the information classifying device. The sample information receiving unit receives the piece of sample information as the object of classification from the information terminal. The distance calculating unit calculates distance information between each of an arbitrary number of pieces of sample information including sample information as an object of classification received by the sample information receiving unit and center of gravity of each of the arbitrary number of populations including the sample information, using a distance evaluation function.

The statistical information calculating unit calculates statistical information, using mean of sample distances and variance of sample distances with the mean of sample distances being the center, based on each group of distance information constituted by the distance information calculated by the distance calculating unit, associated with each sample information belonging to each population. The degree of assignment relevancy evaluating unit evaluates degree of assignment relevancy by calculating distance between the center of gravity of each population and sample information as an object of classification using the distance calculating unit, and normalizing the distance using the statistical information calculated by the statistical information calculating unit on the calculated distance and performing a statistical test.

The assignment destination determining determines to which population the piece of information as the object of classification is to be assigned, in accordance with the degree of assignment relevancy determined by the degree of assignment relevancy determining unit. The population identifying information passing unit passes population identifying information identifying the population determined by the assignment destination determining unit to the information terminal. The population identifying information receiving unit receives the population identifying information from the information classifying device.

According to the present invention, an information classifying system is obtained which can provide information for identifying a population to which the piece of sample information as the object of classification belongs in an autonomous and stable manner.

According to a still further aspect, the present invention provides an information providing system used for an information providing service, including an information classifying device and an information terminal connected to the information classifying device through a communication line. The information classifying device includes a sample information receiving unit, a distance calculating unit, a statistical information calculating unit, a degree of assignment relevancy evaluating unit, an assignment destination determining unit, and a population identifying information passing unit. The information terminal includes a sample information passing unit and a population identifying information receiving unit.

The sample information passing unit passes the sample information as the object of classification to the information classifying device. The sample information receiving unit receives the piece of sample information as the object of classification from the information terminal. The distance calculating unit calculates, distance information between each of an arbitrary number of pieces of sample information including sample information as an object of classification received by the sample information receiving unit and center of gravity of each of the arbitrary number of populations including the sample information, using a distance evaluation function.

The statistical information calculating unit calculates statistical information using mean of sample distances and variance of sample distances with the mean of sample distances being the center, based on each group of distance information constituted by the distance information calculated by the distance calculating unit, associated with each sample information belonging to each population. The degree of assignment relevancy evaluating unit evaluates degree of assignment relevancy by calculating distance between the center of gravity of each population and sample information as an object of classification using the distance calculating unit, and normalizing the distance using the statistical information calculated by the statistical information calculating unit on the calculated distance and performing a statistical test.

The assignment destination determining unit determines to which population the piece of information as the object of classification is to be assigned, in accordance with the degree of assignment relevancy determined by the degree of assignment relevancy determining unit. The population identifying information passing unit passes population identifying information identifying the population determined by the assignment destination determining unit to the information terminal. The population identifying information receiving unit receives the population identifying information from the information classifying device.

According to the present invention, information providing service can be realized which uses the information classifying system capable of providing information for identifying a population to which the piece of sample information as the object of classification belongs in an autonomous and stable manner.

According to a still further aspect of the present invention, an information classifying system classifying classified populations recorded on a computer readable recording medium includes an information classifying device, and an information terminal connected to the information classifying device through a communication line. The information classifying device includes a population receiving unit, a distance calculating unit, a statistical information calculating unit, a degree of assignment relevancy evaluating unit, an assignment destination determining unit, a sample information classifying unit, and a classified population passing unit. The information terminal includes a population passing unit and a classified population receiving unit.

The population passing unit passes an arbitrary number of populations containing pieces of sample information to the information classifying device. The population receiving unit receives the arbitrary number of populations containing the pieces of sample information, from the information terminal. The distance calculating unit calculates distance information between each of an arbitrary number of pieces of sample information included in the populations received by the population receiving unit and center of gravity of each of the arbitrary number of populations, using a distance evaluation function.

The statistical information calculating unit calculates statistical information using mean of sample distances and variance of sample distances with the mean of sample distances being the center, based on each group of distance information constituted by the distance information calculated by the distance calculating unit, associated with each sample information belonging to each population. The degree of assignment relevancy evaluating unit evaluates degree of assignment relevancy by calculating distance between the center of gravity of each population and sample information as an object of classification using the distance calculating unit, and normalizing the distance using the statistical information calculated by the statistical information calculating unit on the calculated distance and performing a statistical test.

The assignment destination determining unit determines to which population the piece of information as the object of classification is to be assigned, in accordance with the degree of assignment relevancy determined by the degree of assignment relevancy determining unit. The sample information classifying unit assigns and classifying the piece of sample information as the object of classification to the population determined by the assignment destination determining unit.

The classified population passing unit passes a classified population to which the piece of sample information as the object of classification has been assigned and classified by the sample information classifying unit to the information terminal. The classified population receiving unit receives the classified population from the information classifying device.

According to the present invention, a computer readable recording medium recording classified populations classified by the information classifying system allowing provision of populations to which pieces of sample information are classified in autonomous and stable manner can be provided.

According to a still further aspect, the present invention provides an information classifying system used for searching for a population to which the sample information as the object of classification belongs from an arbitrary number of populations stored in a database, including an information classifying device and an information terminal connected to the information classifying device through a communication line. The information classifying device includes a sample information receiving unit, a distance calculating unit, a statistical information calculating unit, a degree of assignment relevancy evaluating unit, an assignment destination determining unit, and a population identifying information passing unit. The information terminal includes a sample information passing unit and a population identifying information receiving unit.

The sample information passing unit passes the piece of sample information as the object of classification to the information classifying device. The sample information receiving unit receives the piece of sample information as the object of classification, from the information terminal. The distance calculating unit distance information between each of an arbitrary number of pieces of sample information including sample information as an object of classification received by the sample information receiving unit and center of gravity of each of the arbitrary number of populations including the sample information, using a distance evaluation function.

The statistical information calculating unit calculates statistical information using mean of sample distances and variance of sample distances with the mean of sample distances being the center, based on each group of distance information constituted by the distance information calculated by the distance calculating unit, associated with each sample information belonging to each population. The degree of assignment relevancy evaluating unit evaluates degree of assignment relevancy, by calculating distance between the center of gravity of each population and sample information as an object of classification using the distance calculating unit, and normalizing the distance using the statistical information calculated by the statistical information calculating unit on the calculated distance and performing a statistical test.

The assignment destination determining unit determines to which population the piece of information as the object of classification is to be assigned, in accordance with the degree of assignment relevancy determined by the degree of assignment relevancy determining unit. The population identifying information passing unit passes population identifying information identifying the population determined by the assignment destination determining unit to the information terminal.

The population identifying information receiving unit receives the population identifying information from the information classifying device.

According to the present invention, using the information classifying system allowing provision of populations to which pieces of sample information are classified in autonomous and stable manner, a database storing said arbitrary number of populations for searching for a population to which the sample information as the object of classification belongs can be provided.

Preferably, the piece of sample information as the object of classification is an arbitrary vector information, matrix information or tensor information with an identifier allotted beforehand to each element; the distance evaluation function is a function having the vector information, matrix information or tensor information of a prescribed element configuration with an identifier allotted beforehand to each element; and the distance calculating unit calculates the distance information by reconfiguring each element of the arbitrary vector information, matrix information or tensor information such that the identifier of each element of the arbitrary vector information, matrix information or tensor information becomes the same as the identifier of the element of the prescribed element configuration, and inputting to the distance evaluation function.

According to the present invention, identifiers of elements of arbitrary vector information, matrix information or tensor information are respectively re-configured to be the same identifier as the identifiers of elements of prescribed element configuration of the vector information, matrix information or tensor information to be input to the distance evaluation function and input to the distance evaluation function. Therefore, an information classifying device, an information classifying system, an information providing service using the information classifying system, a computer readable recording medium storing classified populations classified by the information classifying system, and a database storing said arbitrary number of populations for searching for a population to which said sample information as the object of classification belongs using the information classifying system, capable of evaluating pieces of sample information of different element configurations with each other, can be provided.

Further, for these elements, evaluation function or samples may be formed using features, names or identifiers in an arbitrary field, and state of assignment of the sample to the population may be evaluated or, the evaluation function of these may be configured or reconfigured.

Preferably, the piece of sample information as the object of classification is an arbitrary vector information, matrix information or tensor information with an identifier allotted beforehand to each element; the distance evaluation function is a function having the vector information, matrix information or tensor information of a prescribed element configuration with an identifier allotted beforehand to each element; and in the step of calculating the distance information, the distance information is calculated by reconfiguring each element of the arbitrary vector information, matrix information or tensor information such that the identifier of each element of the arbitrary vector information, matrix information or tensor information becomes the same as the identifier of the element of the prescribed element configuration, and inputting to the distance evaluation function.

According to the present invention, identifiers of elements of arbitrary vector information, matrix information or tensor information are respectively re-configured to be the same identifier as the identifiers of elements of prescribed element configuration of the vector information, matrix information or tensor information to be input to the distance evaluation function and input to the distance evaluation function. Therefore, an information classifying method, and an information classifying program capable of evaluating pieces of sample information having different element configurations with each other can be provided.

Preferably, identifiers are applied to feature vectors, matrix and/or tensor elements, elements of matching identifiers are organized as features for evaluation and applied to the evaluation function, or distance between vectors, matrixes and/or tensors is evaluated.

Preferably, the distance calculating unit has a function of making apparent element number equal to the element identifiers, by interchanging order of element items of vectors, matrixes and/or tensors, by substituting an element mean value or 0 for a missing element, or by removing an excessive element.

It becomes possible to evaluate vectors, matrixes and/or tensors having partially different elements to each other, or to evaluate vectors, matrixes and/or tensors and evaluation function, using probability of assignment based on the distance from the center of gravity of a population, mean and standard deviation, and therefore, scope of application of evaluation function for the vectors, matrixes and/or tensors becomes wider.

DESCRIPTION OF THE REFERENCE SIGNS

Figure 1:
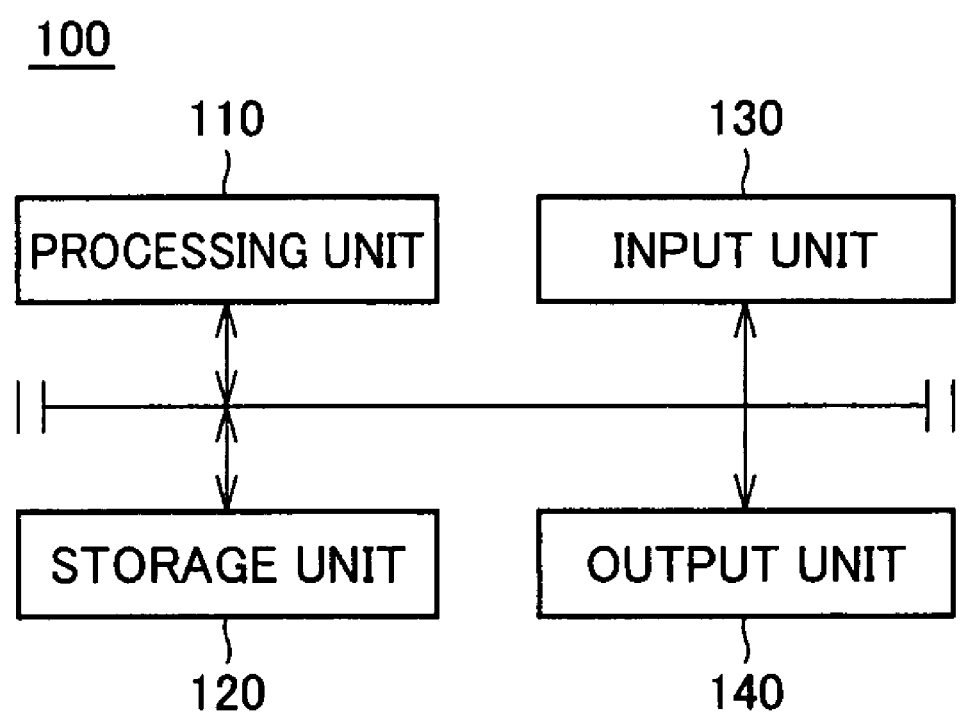
FIG. 1 shows a schematic configuration of the information classifying device in accordance with an embodiment.

100 information classifying device, 100A, 100B information processing device, 110 processing unit, 120 storage unit, 130 input unit, 140 output unit, 200A-200C information terminal, 500 network.

BEST MODES FOR CARRYING OUT THE INVENTION

In the following, embodiments of the present invention will be described in detail with reference to the figures. Throughout the figures, the same or corresponding portions are denoted by the same reference characters and description thereof will not be repeated.

FIG. 1 shows a schematic configuration of an information classifying device 100 in accordance with an embodiment.

Referring to FIG. 1, information classifying device 100 is configured of a computer such as a PC (Personal Computer), and includes a processing unit 110, a storage unit 120, an input unit 130 and an output unit 140. Processing unit 110, storage unit 120, input unit 130 and output unit 140 are connected by a bus, and exchange necessary data through the bus.

Implementation of information classifying device is not limited to a general device such as a PC, and it may be formed as a dedicated device.

Processing unit 110 is configured to include an operating circuitry such as a CPU (Central Processing Unit), MPU (Micro Processing Unit) or a DSP (Digital Signal Processor), and its peripheral circuitry.

Storage unit 120 is implemented by a storage circuitry such as an ROM (Read Only Memory), an RAM (Random Access Memory) or a hard disk. Storage unit 120 is used for storing a program to be executed by information classifying device 100, or used as a work area when the program is executed.

Input unit 130 is implemented by an input device such as a keyboard or a mouse, an image pick-up device such as a camera, or a sound collecting device such as a microphone. Input unit 130 passes the data input through the input device, the image pick-up device or the sound collecting device, to processing unit 110.

Output unit 140 is implemented by a display device such as a display or an acoustic device such as a speaker. Output unit 140 outputs the data received from processing unit 110.

Processing unit 110 executes a prescribed process based on the program stored in storage unit 120, using storage unit 120 as a work area. Further, processing unit 110 receives prescribed data from input unit 130 in accordance with the process. Further, processing unit 110 passes prescribed data to output unit 140 in accordance with the process.

Figure 2:
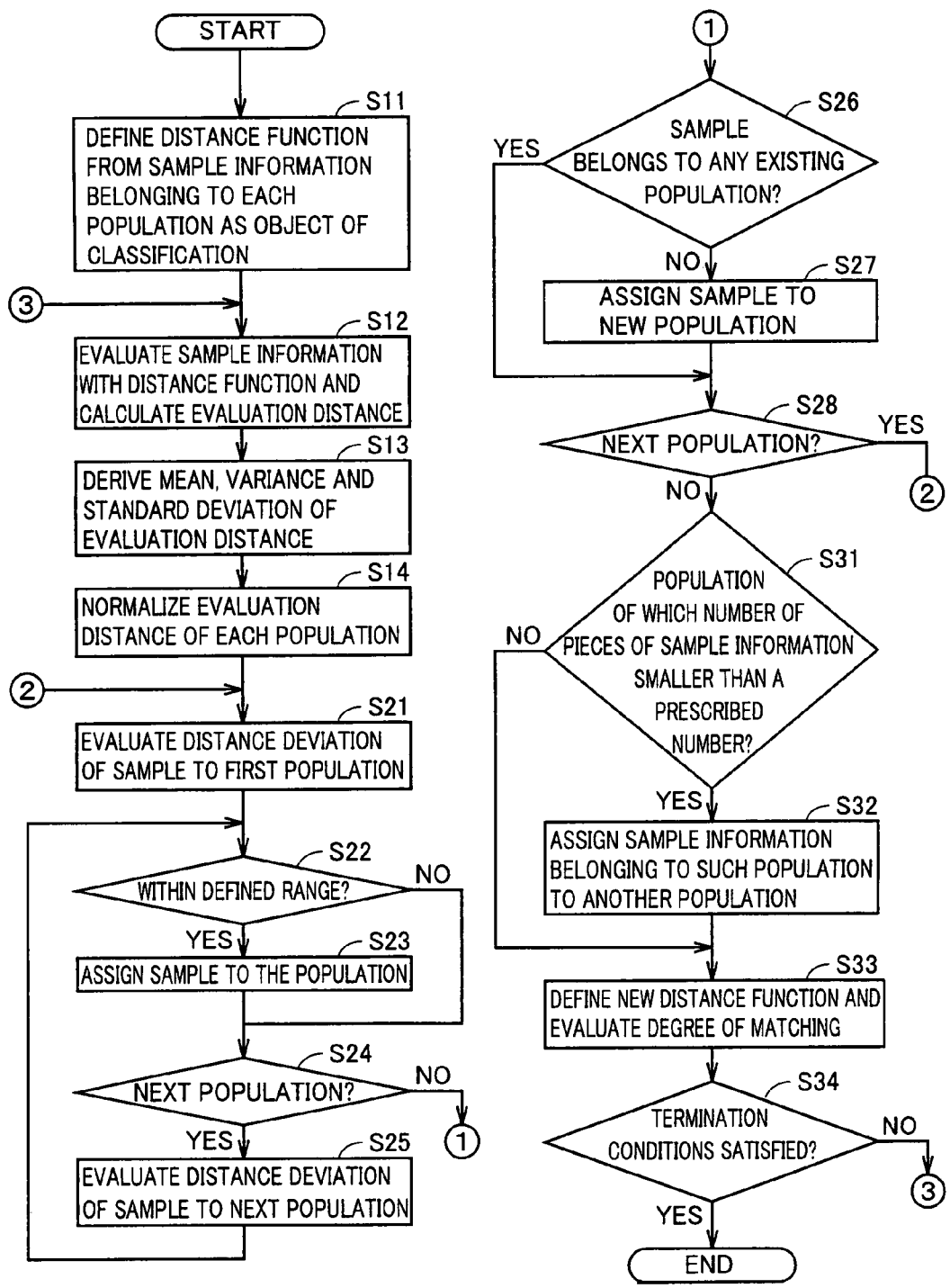
FIG. 2 is a flowchart representing the flow of information classifying process executed by the information processing device of the embodiment.

FIG. 2 is a flowchart representing the flow of information classifying process executed by information classifying device 100 in accordance with the present embodiment.

Referring to FIG. 2, first, at step S11, processing unit 110 forms a distance function from sample information belonging to each of the populations as the object of classification stored in storage unit 120.

Specifically, certain populations $A(a_1, a_2, \ldots, a_n)$ and $B(b_1, b_2, \ldots, b_m)$ and sample information groups $a_1, a_2 \ldots, a_n$ and $b_1, b_2, \ldots, b_m$ forming these will be described. Here, $a_n$ and $b_m$ may be multi-dimensional vectors, matrixes or tensors.

Processing unit 110 obtains, from these sample information groups, variables for multivariate analysis of respective populations A and B, such as eigen values, eigen vectors, mean values or standard deviations.

Based on the variables for covariance structural analysis obtained here, processing unit 110 forms, using pieces of sample information $a_n$ and $b_m$ as augment $$\vec{X},$$ [Expression 1]

distance functions $$F_a(\vec{X})$$ [Expression 2]

and $$F_b(\vec{X})$$ [Expression 3]

in order to find Mahalanobis distance between each sample information and populations A, B.

In the distance functions, if the augment $$\vec{X}$$ [Expression 4]

is a vector, accuracy of result of operation may be set using an evaluating variable such as represented by the evaluation dimension number, which is an internal variable of the distance evaluation function, and the accuracy may be designated to an arbitrary value.

Mahalanobis distance is represented by the following equation.

$$D_{i,k} = F_i(\vec{X}_k) = \sqrt{(\vec{X}_k - \vec{\mu}_i)^T V_i^{-1} (\vec{X}_k - \vec{\mu}_i)}$$ [Expression 5]

Here, i represents a value for identifying a plurality of populations, k represents a value for identifying a sample, and $D_{ik}$ represents distance between a sample k and the center of gravity of a population i, in accordance with the distance function $$F_i(\vec{X}_k).$$ [Expression 6]

Further, m represents mean vector obtained from sample information.

$$\vec{x}$$ [Expression 7]

represents sample information vector.

In Expressions 5 and 9, $V_i$ represents covariance matrix of population i.

By a representation using eigen value and eigen vector, it will be given as $$D_{ik} = F_i(\vec{X}_k) = \sqrt{\sum_{j=1}^{n} \frac{\left((\vec{X}_k - \vec{\mu}_i)^T \phi_{ij}\right)^2}{\lambda_{ij}}}$$ [Expression 8]

Here, $f_i$ represents eigen vector of covariance matrix of the population.

$\lambda_i$ represents eigen value of covariance matrix of the population.

Further, by adding a constant $\log|V_i|$ based on the eigen value and prior probability $\log P(_{wi})$ to Mahalanobis distance, a multi-dimensional distance calculating function based on Bayesian discrimination function can be defined, which is given as $$g_i(\vec{X}_k) = -\frac{1}{2}\left((\vec{X}_k - \vec{\mu}_i)^T V_i^{-1}(\vec{X}_k - \vec{\mu}_i) + \log|V_i|\right) + \log P(\omega_i)$$ [Expression 9]

Another possible expression is as follows.

$$g_i(\vec{X}_k) =$$ [Expression 10]

$$-\frac{1}{2}\left(\sum_{j=1}^{n} \frac{\left((\vec{X}_k - \vec{\mu}_i)^T \phi_{ij}\right)^2}{\lambda_{ij}} + \log\prod_{j=1}^{n} \lambda_{ij}\right) + \log P(\omega_i)$$

Here, the term $\log P(_{wi})$ appended at the last part represents correction based on prior probability, and therefore, it may be removed for the purpose of improving performance, to realize evaluation with uniform probability on every population, or a correction value based on transition probability or output probability may be applied for adjusting the evaluation result based on preceding/succeeding state of distance evaluation.

Then, the value corresponding to the distance from the center of gravity can be derived in the form of $$D_{ik}^2 = -g_i^2(\vec{X}_k)$$ [Expression 11]

Next, at step S12, processing unit 110 evaluates the sample information with the distance functions formed at step S11, and calculates evaluation distance. At step S13, processing unit 110 derives sample mean, sample variance and standard deviation of samples of each group of evaluation distances calculated at step S12.

Specifically, for the formed distance function $$F_a(\vec{X})$$ [Expression 12]

sample information group $a_1, a_2, \ldots, a_n$ is input and for the distance function $$F_b(\vec{X})$$ [Expression 13]

sample information group $b_1, b_2, \ldots, b_m$ is input. As a result, pieces of distance information $D_{a1}, D_{a2}, \ldots, D_{an}, D_{b1}, D_{b2}, \ldots, D_{bm}$ based on distance functions are obtained. From the group Da of population A and the group Db of population B obtained in this manner, statistical information containing respective mean distance values $\mu D_a$ and $\mu D_b$ and distance standard deviations $\sigma D_a$ and $\sigma D_b$ is calculated. Here, the value for identifying group a or b is input as i of Expressions above.

$$\mu D_a = n^{-1} \sum_{k=0}^{n} D_{ak}$$ [Expression 14]

$$\sigma D_a = \sqrt{n^{-1} \sum_{k=0}^{n} (D_{ak} - \mu D)^2}$$ [Expression 15]

Next, at step S14, processing unit 110 normalizes the evaluation distance of each population calculated at step S12.

Specifically, to distance function $$F_a(\vec{X}_{ak})$$ [Expression 16]

sample information groups $a_1, a_2, \ldots, a_n$ and $b_1, b_2, \ldots, b_m$ are input, and resulting evaluation distance group $D_a$ is normalized by $\mu D_a$ and $\sigma D_a$. Similarly, to the distance function $$F_b(\vec{X}_{bk})$$ [Expression 17]

sample information groups $a_1, a_2, \ldots, a_n$ and $b_1, b_2, \ldots, b_m$ are input, and resulting evaluation distance group $D_b$ is normalized by $mD_b$ and $\Box D_b$. As a result, distance deviations $V_{a1}, V_{a2}, \ldots, V_{an}, V_{b1}, V_{b2}, \ldots, V_{bm}$ of respective samples calculated using the mean distance from the center of gravity of each sample group, based on the evaluation functions formed from the samples belonging to respective populations, are obtained.

$$V_{ak} = \sigma D_a^{-1}(D_{ak} - \mu D_a)$$ [Expression 18]

$$V_{bk} = \sigma D_b^{-1}(D_{bk} - \mu D_b)$$ [Expression 19]

Next, at step S21, processing unit 110 evaluates the distance deviation of the sample to the first population calculated at step S14. Then, at step S22, processing unit 110 determines whether the distance deviation is within a defined range or not.

If the distance deviation is within the defined range (YES at step S22), processing unit 110 assigns the sample to the population at step S23, and the process proceeds to step S24. If the distance deviation is not within the defined range (NO at step S22), the process proceeds to step S24.

At step S24, processing unit 110 determines whether there is a next population. If there is a next population (YES at step S24), processing unit 110 evaluates distance deviation of the sample to the next population at step S25, and the process returns to step S22. If there is not the next population (NO at step S24), the process proceeds to step S26.

At step S26, processing unit 110 determines whether the sample has been assigned to any of the existing populations or not. If it is not assigned to any of the populations (NO at step S26), processing unit 110 generates a new population at step S27 and assigns the sample to the population, and the process proceeds to step S28. If the sample has been assigned to any of the populations (YES at step S26), the process proceeds to step S28.

Specifically, when distance deviation $V_{ak}$ of distance function $F_a(a_k)$ for sample $a_k$ is smaller than 3s, the sample is assigned to population A.

When distance deviation $V_{ak}$ of distance function $F_a(a_k)$ is not smaller than $3\sigma$, and distance deviation $V_{ak}$ of $F_b(a_k)$ is smaller than $3\sigma$, for sample $a_k$, the sample is assigned to population B.

When distance deviation $V_{ak}$ of distance function $F_a(a_k)$ is not smaller than $3\sigma$, and distance deviation $V_{ak}$ of $F_b(a_k)$ is not smaller than $3\sigma$, for sample $a_k$, a new population C is generated, and the sample is assigned to population C.

$$\begin{cases} \vec{A} \cup a_k & (\text{when } V_{ak} < 3\sigma_a) \\ \vec{B} \cup a_k & (\text{when } V_{ak} > 3\sigma_a \wedge V_{ak} < 3\sigma_b) \\ \vec{C} \cup a_k & (\text{when } V_{ak} > 3\sigma_a \wedge V_{ak} > 3\sigma_b) \end{cases} \quad \text{[Expression 20]}$$

Then, at step S28, processing unit 110 determines whether there is a next sample. When there is a next sample (YES at step S28), processing unit 110 returns the process to step S21. When there is not a next sample (NO at step S28), processing unit 110 proceeds to the process at step S31.

Specifically, steps S21 to S27 are executed on pieces of sample information $a_1$ to $a_n$. Similarly, steps S21 to S27 are executed on pieces of sample information $b_1$ to $b_m$.

Specifically, when distance deviation $V_{bk}$ of distance function $F_b(b_k)$ for sample $b_k$ is smaller than 3s, the sample is assigned to population B.

When distance deviation $V_{bk}$ of distance function $F_a(b_k)$ is smaller than 3□, and distance deviation $V_{bk}$ of $F_b(b_k)$ is not smaller than $3\sigma$, for sample $b_k$, the sample is assigned to population A.

When distance deviation $V_{bk}$ of distance function $F_a(b_k)$ is not smaller than $3\sigma$, and distance deviation $V_{bk}$ of $F_b(b_k)$ is not smaller than $3\sigma$, for sample $b_k$, a new population C is generated, and the sample is assigned to population C.

$$\begin{cases} \vec{B} \cup b_k & (\text{when } V_{bk} < 3\sigma_b) \\ \vec{A} \cup b_k & (\text{when } V_{bk} > 3\sigma_a \wedge V_{bk} < 3\sigma_b) \\ \vec{C} \cup b_k & (\text{when } V_{bk} > 3\sigma_a \wedge V_{bk} > 3\sigma_b) \end{cases} \quad \text{[Expression 21]}$$

It is also possible to assign a sample belonging to population A or B to a population of which standard deviation of distance is the smallest.

Here, the reference of three times s used as an index here represents a value that is expected to cover 99.7% of samples in considering probability of assignment, probability of appearance or probability of belonging derived from statistical probability density function, and an arbitrary magnification may be used taking into account the specification, idea or purpose of the device.

A method of selecting a population to which the sample is to be assigned, by combining an approach in which an arbitrary value of $\sigma$ is used as an evaluation standard, an approach in which whether a sample up to an arbitrary order is within $3\sigma$ or not is evaluated, an approach in which a sample assigned to a population closest to the center of gravity is evaluated, an approach in which a sample assigned to a population closest to the mean distance is evaluated, and an approach in which the evaluation distance has a negative value and the sample is evaluated as belonging to a population when probability is not smaller than 1 if the distance is considered as an exponent part, may be used as the method of classification here.

The value serving as the position of the center of gravity for the population itself may be given as $$\mu D_a = \frac{1}{2} \log \prod_{k=0}^{n} \lambda_{ak} - \log P(\omega_a) \quad \text{[Expression 22]}$$

$$\mu D_a = \frac{1}{2} \log \prod_{k=0}^{n} \lambda_{ak} \quad \text{[Expression 23]}$$

By using the value represented by Expression 22 or Expression 23 as a mean, standard deviation of the distances of the group of samples from the center of gravity may be calculated, to be used as the boundary reference of the method described above. Here, not the mean distance but the distance from the center of gravity of the population is used as the evaluation reference. Therefore, a distance defining the boundary of assignment may be determined using the probability of appearance, probability of assignment or probability of belonging calculated from statistical probability density function, in accordance with the mean $\mu D_a$ calculated from a constant based on the eigen value and standard deviation $\sigma D_a$ based on the mean.

Assuming a normal distribution, mean distance value of samples from the center of gravity of the population is statistically expected to be around $0.68\sigma$. Therefore, a sample of which value is not higher than $-0.68\sigma$ from the mean distance value is also considered to have a characteristic different from the population. Therefore, the population to which it belongs may be changed, and it may be determined based on probability density function of other distribution such as gamma distribution.

When the method of classification based on the mean distance value and the standard deviation is used, it is possible to designate conditions of re-classification by combining arbitrary conditions and a plurality of populations. Here, if a sample is sufficiently close to centers of gravity of the plurality of populations, one which is closer may be selected, the sample may be assigned to one that has smaller standard deviation, or when both are small, a new population may be generated, the sample may be assigned to both populations, or the method of classification may be changed dependent on positive/negative deviation, and the configuration may allow arbitrary selection of these methods.

Next, at step S31, processing unit 110 determines whether there is any population of which number of pieces of sample information is smaller than a prescribed number, for example, smaller than 200, or not. If there is a population of which number of pieces of sample information is smaller than the prescribed number (YES at step S31), processing unit 110 assigns pieces of sample information belonging to that population to another population. In other words, such a population is removed. Thereafter, processing unit 110 proceeds to the process of step S33. When there is no population of which number of pieces of sample information is smaller than the prescribed number (NO at step S31), processing unit 110 proceeds to the process of step S33.

It is preferred that the pieces of sample information belonging to the population to be removed are assigned to a population having the smallest standard deviation of distance. Alternatively, only the removal of the population may be done and the pieces of sample information belonging to the population to be removed may not be assigned to any other population and used simply as the pieces of sample information for obtaining distance and tentative population to which the sample is to be assigned, based on the distance function at step S33.

Next, at step S33, processing unit 110 forms a distance function for the re-classified population, and evaluates whether classification has been done in an appropriate manner or not based on recognition by a determination function using the distance function. Then, at step S34, processing unit 110 determines whether repeated evaluation of the degree of matching satisfies termination conditions or not and determines whether the process is to be continued by repeating classification.

Here, whether the terminating conditions are satisfied or not may be determined base on whether increase/decrease of the number of populations has attained to a designated value or lower, whether it has attained to a designated ratio or lower, whether the standard deviation and mean distance of each sample have attained to a prescribed ratio or not, in the result of reevaluation based on mean, variance, standard deviation, eigen value and eigen vector of latest populations, whether the samples belonging to the original population have attained to a prescribed value or higher, whether the variance of standard deviation itself obtained from a group of evaluation distances has attained to a prescribed value or lower, or whether it attains to a prescribed ratio with respect to a mean value of evaluation distance or not.

When the terminating conditions are not satisfied (NO at step S34), processing unit 110 returns to the process of step S12, and processes from steps S12 to S32 are executed recursively. When the terminating conditions are satisfied (YES at step S34), processing unit 110 terminates the information classifying process.

Figure 3:
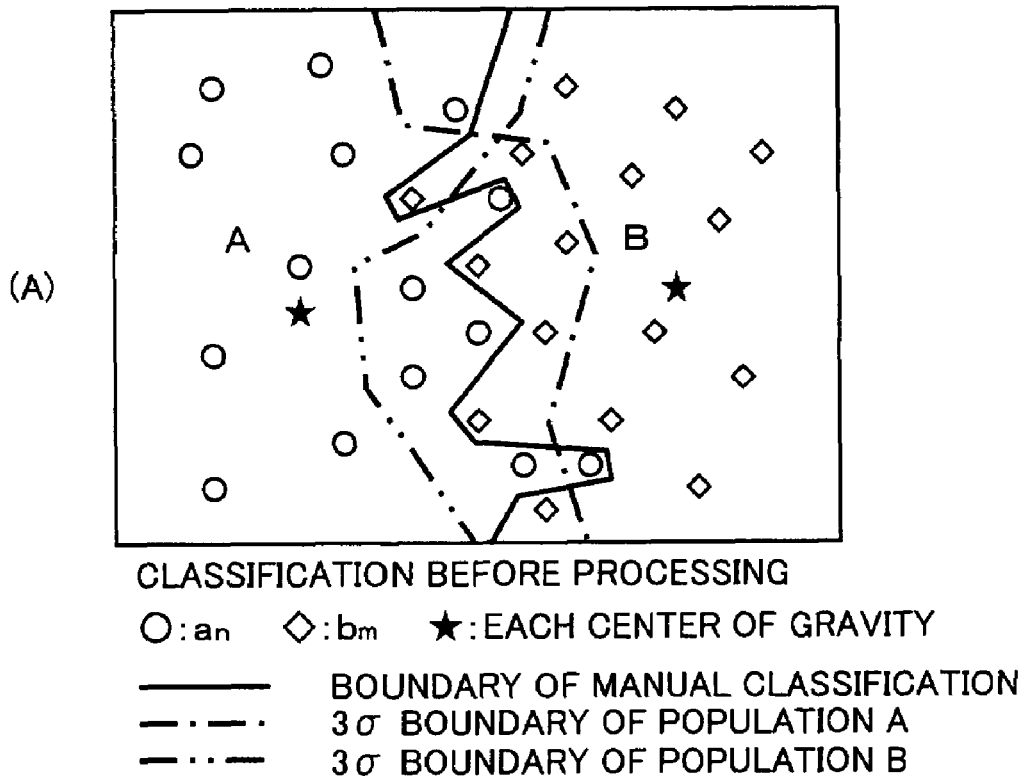
FIG. 3 shows an example of populations in the information classifying process in accordance with supervised learning of the embodiment.
Figure 3:
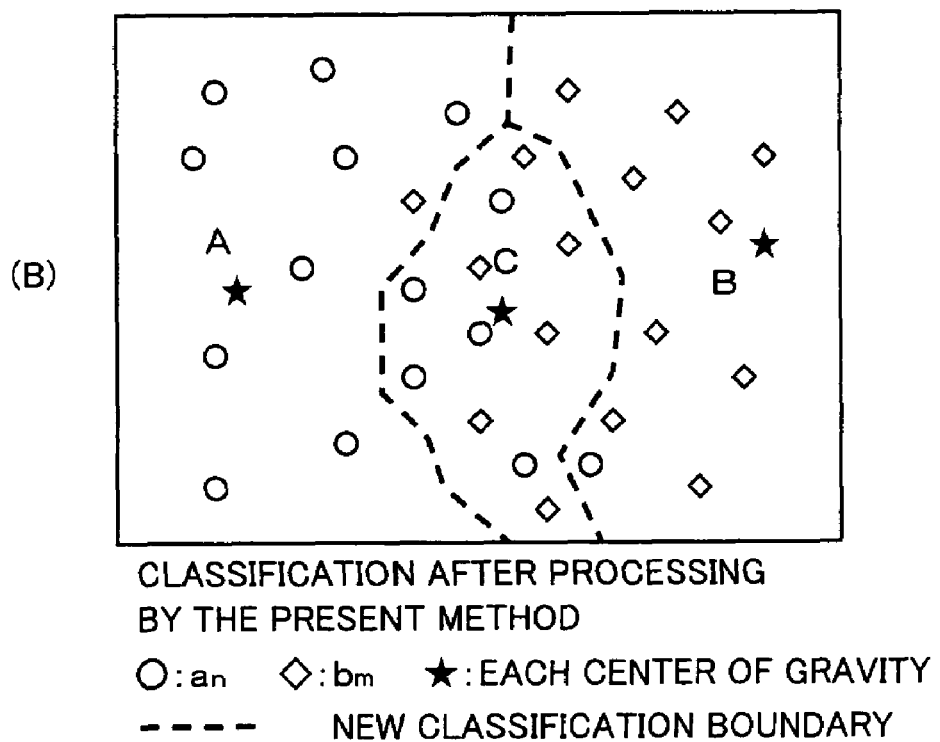

FIG. 3 shows examples of populations in the information classifying process based on supervised learning in accordance with the present embodiment.

FIG. 3(A) shows classification of populations before the information classifying process. Referring to FIG. 3(A), in this figure, pieces of sample information $a_n$ and $b_n$ are plotted as a scatter diagram. Sample information $a_n$ is represented by "○" and sample information $b_n$ is represented by "◇". Here, a person classifies the sample information to a and b, determining the contents. A set of pieces of sample information $a_n$ constitutes population A, and a set of pieces of sample information $b_n$ constitutes population B.

Centers of gravity of populations A and B before classification are represented by "≪". The 3σ boundary of population A before classification is represented by a one-dotted chain. The 3σ boundary of population B before classification is represented by a two-dotted chain. As can be seen, when the pieces of sample information classified by a person determining the contents of the sample information are plotted, the boundary of classification between a and b is staggered.

FIG. 3(B) shows classification of populations after the information classifying process. The new boundary of classification of populations after processing is given by dotted lines. The center of gravity of a newly generated population C is also represented by "★", similar to the centers of gravity of populations A and B.

In this manner, through the information classifying process, pieces of information of which distance obtained based on a plurality of distance functions is apart from the statistical distance from the center of gravity of the population may form a unique population, or may be assigned to the population of which center of gravity is closer. Thus, even when there are pieces of information near the boundary, which are prone to human evaluation error, the distribution close to a normal distribution can be attained, and a stable population can be formed in an autonomous manner.

Next, results of an experiment will be described.

This experiment was conducted for the purpose of confirming, above all, that an efficient classification can be realized, as understood from the fact that the matching ratio of pre-classification and post-classification based on the result of recognition increases and the number of classifications is reduced, using human phonetic information as an example of natural information of which classification has been difficult, as the sample information.

The phonetic information is as follows: the number of dimensions per one sample is 192 dimensions, the number of representative initial populations at the start, designated manually, is 8, the number of data samples is about 250,000 and the uttered phonemes are of 28 types.

When the number of samples of a newly formed population is smaller than 200 samples that is approximately the same as the number of evaluation dimensions necessary for evaluating distance in accordance with Bayesian discrimination function, the population is not maintained, from statistical reasons.

In this experiment, by the information classifying process described above, first, 28 types of phonemes are classified to 8 different populations based on subjective phonetic conditions of a specific person. Assume that samples belonging to respective populations have been labeled before evaluation, and a population, to which a sample is determined to belong based on the label, matches a population having a label of closest distance after evaluation. When the distance to the center of gravity of the matched population containing the sample of interest is smaller than 3s from the mean distance of the population to which it belongs, the sample is assigned to the population before evaluation.

Next, assume that the population to which a sample has belonged before evaluation matches the population of the shortest distance obtained after evaluation. Here, if the distance is larger by 3σ or more from the mean distance of the population before evaluation or the distance to a center of gravity of another population is larger by 3σ or more from the mean distance of each population, a new population is formed.

When the population to which a sample has belonged before evaluation does not match the population of the shortest distance obtained after evaluation and the distance of the sample is within the range of 3σ from the mean distance of another population, the sample is assigned to the matching population, and when it is larger by 3σ or more from the mean, a new population is formed.

Figure 4:
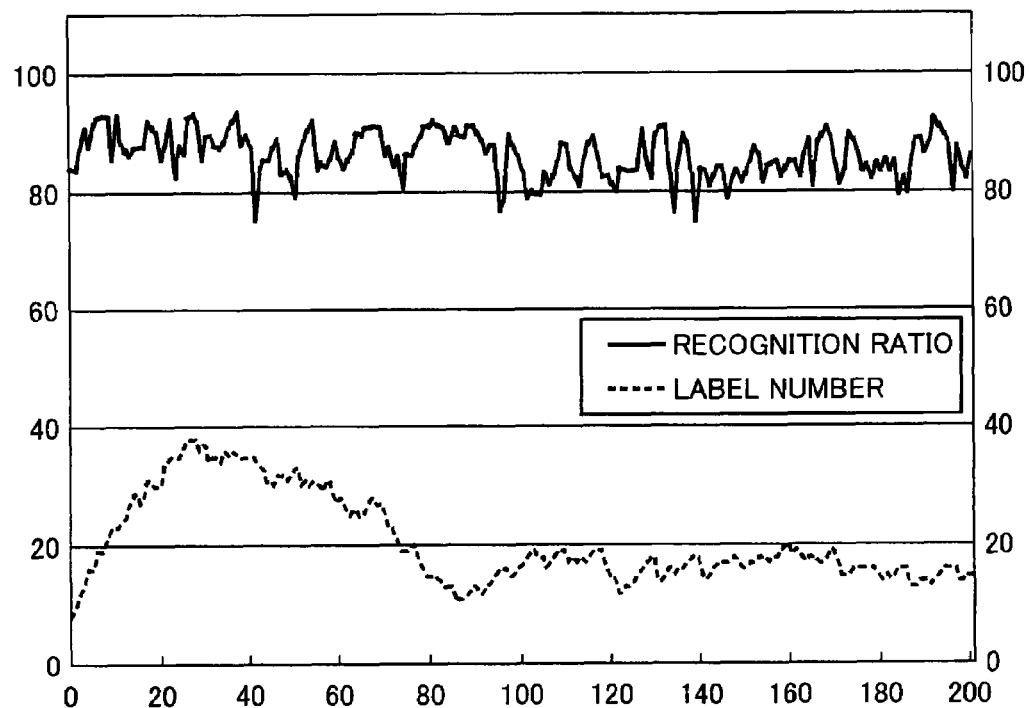
FIG. 4 is a graph representing results of an experiment of information classification based on supervised learning in accordance with the embodiment.
Figure 5:
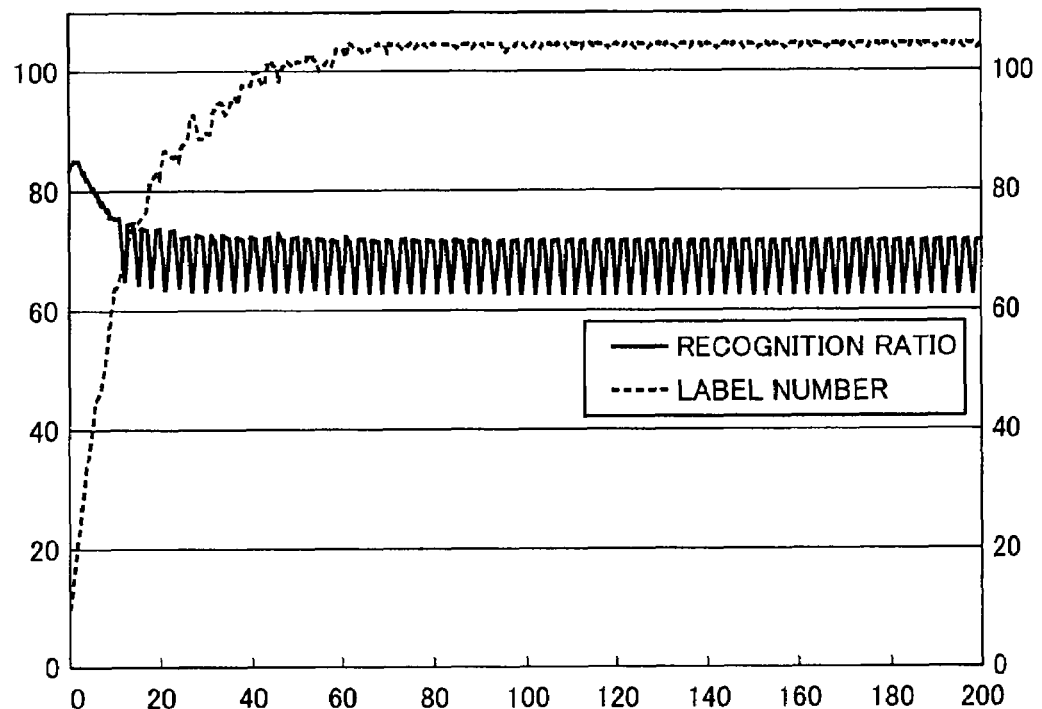
FIG. 5 is a graph representing results of a controlled experiment of information classification.

FIG. 4 is a graph representing the results of experiment of information classification based on supervised learning in accordance with the present embodiment. FIG. 5 is a graph representing the results of a control experiment of information classification. The ordinate represents the number of populations and matching ratio. The abscissa represents the number of iterations of the information classifying process.

It can be seen from FIG. 4 showing the results of the present experiment, that the number of populations increases temporarily to around 40 and then, the number of populations gradually settles through increase/decrease around 16 to 20 and is stabilized, and the matching ratio starts from about 80% and, though lowers from time to time, the ratio of 80% or higher is stably maintained.

Referring to FIG. 5, in the control experiment, a method is adopted in which if the population to which the sample belongs before evaluation does not match the population of the closest distance after evaluation, a new population is formed, and when the populations match, the assignment is not changed.

Therefore, the number of populations increases gradually, and the number of populations stops around 105 where collection of sufficient samples becomes difficult. Further, the recognition ratio, which was 80% at the start decreases to the range of 72% to 62%, and hence, it can be seen that stable classification was not possible.

Specifically, by the classification experiment shown in FIG. 4, it is possible to classify 250,000 samples into at most 20 populations within 3σ while attaining the recognition ratio of at least 80%. In contrast, in the control experiment of FIG. 5, the number of populations continuously increases up to around 105, where the number of samples becomes smaller than the necessary number of 200 to form a population, and in addition, the recognition ratio lowers to the percentage of 70s. From the foregoing, regardless of the original 28 phonemes, it can be determined that the results of experiment shown in FIG. 4 realized more efficient classification to populations of around 15, than the results of experiment shown in FIG. 5 having populations larger than 100.

Figure 9:
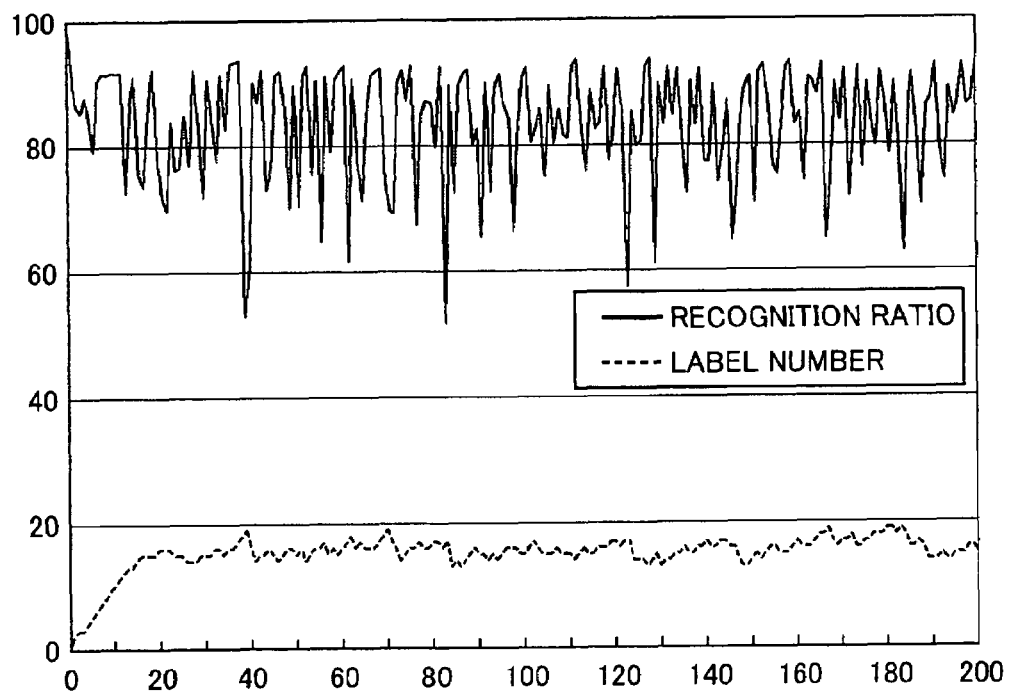
FIG. 9 is a graph representing results of an experiment of information classification based on unsupervised learning with larger number of samples in accordance with the embodiment.

FIG. 9 is a graph representing the results of experiment of information classification in accordance with the present embodiment, for unsupervised learning with larger number of samples.

Referring to FIG. 9, from the results of information classification shown in FIG. 9, even in unsupervised learning with about 2,500,000 samples additionally including about 2,250,000 new samples of the same speaker as FIG. 3, classification to stable populations of about 14 to 18, that is, around the label number 16, close to the prior experiment even after 200 trainings, similar to the experiment in accordance with the present invention using 250,000 samples, was possible.

As described above, information classifying device 100 in accordance with the present embodiment calculates evaluation distance between the center of gravity of pieces of sample information belonging to each of the plurality of populations containing pieces of sample information and the sample information as the object of classification, as described with reference to steps S11 and S12 of FIG. 2.

Further, as described with reference to step S13 of FIG. 2, information classifying device 100 calculates statistical information including mean, variance, standard deviation and the like of the evaluation distance calculated in step S12, for each population.

Further, as described with reference to steps S21 and S25 of FIG. 2, information classifying device 100 evaluates degree of assignment relevancy of the sample information as the object of classification, by evaluating evaluation distance of the sample information to the population, based on the evaluation distance calculated at step S12 and on the statistical information calculated at step S13.

Further, as described with reference to steps S22 to S27 of FIG. 2, information classifying device 100 determines to which population the sample information as the object of classification should be assigned, in accordance with the degree of assignment relevancy evaluated at step S21 or S25.

Further, as described with reference to step S23 and S27 of FIG. 2, information classifying device 100 assigns the sample information as the object of classification to the determined population.

In this manner, by information classifying device 100, the sample information as the object of classification is assigned to any of the populations in accordance with the degree of assignment relevancy to the population. As a result, stable classification of the sample information to a population in an autonomous and stable manner becomes possible.

Further, as described with reference to step S33 of FIG. 2, information classifying device 100 calculates the evaluation distance between the center of gravity of each updated population to which the sample information as the object of classification has been assigned, and the sample information as the object of classification belonging to each of the updated population, and recursively executes steps S12 to S33, whereby the sample information as the object of classification is assigned to any of the populations in accordance with the degree of assignment relevancy, based on the calculated evaluation distance.

As a result, by information classifying device 100, the sample information can further be classified to a population in a recursive manner.

Further, as described with reference to steps S26 and S27 of FIG. 2, when the degree of assignment relevancy to every population is out of a prescribed range, that is, when the deviation of evaluation distance from a mean value for every population is out of the range of 3σ, information classifying device 100 generates a new population, and assigns the sample information as the object of classification to the generated population.

Accordingly, the sample information that belongs to a population is the sample information of which degree of assignment relevancy is within a prescribed range. Specifically, it is possible by information classifying device 100 to classify sample information of which deviation of evaluation distance for the population from the mean value is within the range of 3σ.

As a result, it becomes possible by information classifying device 100 to classify sample information within a range of a prescribed degree for the population. Further, it is possible to classify sample information to populations to have approximately normal distribution in which a prescribed ratio of pieces of sample information belonging to the population are distributed within the range of 3σ from the mean value.

Further, as described with reference to steps S31 and S32 of FIG. 2, information classifying device removes a population that does not contain a prescribed number of pieces of sample information, and the pieces of sample information that have belonged to the removed population are assigned to other population or populations. Thus, irrelevant population is removed.

Further, as described with reference to steps S21 to S27 of FIG. 2, information classifying device 100 may assign the sample information as the object of classification to a population to which degree of assignment relevancy evaluated at step S21 or S25 is the highest.

Consequently, it follows that the sample information as the object of classification is assigned to the population to which evaluated degree of assignment relevancy is the highest, by information classifying device 100. As a result, optimal classification of sample information to the population becomes possible.

Further, as described with reference to step S14 of FIG. 2, information classifying apparatus 100 normalizes the evaluation distance calculated at step S12.

This facilitates handling of evaluation distance by information classifying device 100.

The present embodiment will be summarized in the following.

Using processing unit 110, information classifying device 100 calculates mean and variance for the sample information classified to populations in storage unit 120, forms a covariance matrix, and stores it in storage unit 120.

Next, from the covariance matrix, eigen values and eigen vectors are calculated, classified together with the population to which the sample belongs, and stored as evaluation function, in storage unit 120.

Based on all evaluation functions that are stored, distance calculation for every sample is performed by processing unit 110, classification is done in accordance with the contents, and if necessary, a new population is given and stored in storage unit 120.

In accordance with populations classified using the stored populations, operations for calculating mean, variance and the like are again performed in accordance with a new classification, using processing unit 110, and the operation is repeated until the number of populations is settled.

Next, a modification of the present embodiment will be described.

The range of $3\sigma$ used in the experiment represents the range that covers about 99.7% of the population, and according to statistical expectation, it is expected that good classification is possible with a value around $2\sigma$ that covers 98%, as the test boundary.

Further, as a characteristic of Mahalanobis distance, it has been well known that Mahalanobis distance between the center of gravity of a population and sample information has the number of dimensions of the sample information. Considering this characteristic, it can be understood that a sample at a distance equal to the number of evaluation dimensions from the center of the population is included in $0.68\sigma$.

Therefore, considering the fact that the distance from the center of gravity is an absolute value, the distance that corresponds to $\pm 3\sigma$ is around 4.5 times the number of dimensions of the sample of the obtained distance, and if Mahalanobis distance is smaller than this value, it is expected that the sample belongs to the original population with the probability of 99.7%, and if the value is larger, it is expected that the sample may not belong to the population.

Therefore, an application becomes possible using the present embodiment, in which reclassification to a different population is done through reclassification through the process steps described above.

A method is considered in which samples that are found as a result of classification to be apart by at least 4.5 times from the center of gravity of every existing population are all assigned to one population, and one new population is added.

Further, assume that there are existing populations A, B and C. If a sample that is apart by at least 4.5 times from every population is closest to A, a label A1 is appended, and if it is closest to B, a label B1 is appended, and by appending a label of seemingly high similarity in this manner, similar samples are collected. Thus, a method of classifying samples by allocating new labels including such auxiliary label or labels becomes possible.

Here, when A1 is evaluated to belong to A, such evaluation may be regarded as correct evaluation, and by applying multi-template approach, classification efficiency or classification analysis can be improved.

Further, a method of improving learning efficiency of a population is readily conceived. For example, classification may be done initially with narrow standard of $1\sigma$ or $2\sigma$ and after a few numbers of processes, the width may be widened to $4\sigma$ or $5\sigma$ so that the conditions are changed from strict to mild, enabling improved learning speed.

Further, when the value $\sigma$ as the boundary for classification is to be found, the minimum value $\sigma$ in a negative direction viewed from a mean position based on the mean distance from the center of gravity of a population may be found, or a minimum value $\sigma$ to a sample closest to the center of gravity may be found, and thereafter, the absolute value or square thereof may be used as an upper limit for evaluation of the value $\sigma$ in the positive direction viewed from the mean position. As for the square of a value smaller than the mean distance and closest to the center of gravity of the vector, assuming that the standard deviation from the mean distance to the smallest evaluation distance is $-2$, standard deviation of $+4$ from the mean distance may be regarded as the upper limit range. The magnification and the number of powers may be arbitrarily designated.

As a reverse method, a method is readily conceived in which the initial few times may be performed with the standard set to wider $5\sigma$ and thereafter narrowed to $2\sigma$, to improve learning efficiency of the population. Further, a method is readily conceived, by using a method of stopping increase/decrease of populations when the change in populations decreases, to improve learning efficiency of the population.

Further, in the distance calculation, not only the sample information of a designated range with the mean being the center but also sample information on one side, that is, smaller than or larger than the mean, may be used as a new population, or a new population may be formed by designating an asymmetric range.

Further, a process may be possible, in which, when a plurality of populations are involved in evaluation, by assigning sample information $a_n$ to a closer population that is within an arbitrary range, divided populations may be merged, and the number of population is thus decreased.

It is well known that by a method of obtaining probability value using Mahalanobis distance as an exponent part of natural logarithm, it can be utilized not only as distance evaluation of a simple n-dimensional space but as a probability based on time-sequential statistics. Therefore, the probability value of 0 to 1 may be used as the distance of the present method, or an exponent value may be regarded as the distance, and used for evaluation.

Further, the probability that the sample information belongs to a population is probability of appearance or probability of assignment based on the probability density function and, therefore it naturally assumes 1 if it belongs to the population. The sample information for learning used for recognition and the like, however, is natural information, and involves change in environment or variance due to human interpretation. As a measure to such situation, the present invention may be utilized.

The present method may be applicable to arbitrary AI methods, evaluation functions, classification evaluation methods, various probabilistic evaluation methods, multi-layered models, single-layered models, parallel models, interconnected models, and time-continuous models thereof, distances obtained by using results of evaluation obtained by evaluation models as a combination thereof, or respective input/output parameters or coefficients, including various neural networks, Markov process, boltzmann machine using a probability model such as Bayes estimation, HMM (Hidden Markov Model), Bayesian network, Bayes discrimination function, Neo cognitron, Cognitron, automaton, cellular automaton, fuzzy function, chaos function, fractal function, fluctuation function, learning vector quantization (LVQ), self organizing map (SOM), vector quantization neural network, competitive learning type vector quantization neural network, Hopfield network, perceptron, back propagation learning, Hamming network, Carpenter-Grossberg identifier, multi-valued Hopfield network, parallel Hopfield network, continuous valued Hop field network, interconnection neural network, cellular neural network, fuzzy neural network, single-layer perceptron, multi-layered perceptron Kohonen learning, steepest descent method, forward learning, backward learning, adaptive resonance theory model, state transfer network, recurrent network, Elman network, Jordan network, feature map, combinet, competitive learning, association, error back propagation learning, self organizing feature map, associative memory, dynamical network, counterback propagation, fuzzy inference, genetic algorithm, chaos model, fractal model, and ab-initio method. Further, if a multi-layered model of these is used, distance evaluation of a value used for a combination with an arbitrary input/output variable for one or all of an input layer, an intermediate layer and an output layer may be executed, if a non-hierarchical model is used, an input value of each node or an output value of a firing node may be used, a hierarchical or three-dimensional configuration or higher dimension may be formed by combining such non-hierarchical models, and a value based on a result of evaluation output thereby may be used as the distance.

Further, the present invention may be used as means for classifying groups of information having mixture distribution information or arbitrary distribution information as populations, or forming an optimal evaluation function for evaluating time-sequential transition states, combined with hierarchical Bayes, empirical Bayes, variational Bayes, naïve Bayes, expanded Bayes method, integrated Bayes method, large scale Bayes method, simple Bayes method, Markov chain Monte Carlo (MCMC), annealing, boosting, M-H (Metropolis-Hastings) algorithm, hit-and-run algorithm, Gibbs sampler, SIR method (Sampling/Importance Re-sampling), support vector machine (SVM), EM (Expectation Maximization) algorithm, maximum distance algorithm, principal component analysis (PCA), independent component analysis, KL expansion, K-means, maximum entropy method, back-off weighting or the like.

Further, it is possible to increase speed of access to distance evaluation functions formed in large quantity through hash-buffer processing, by utilizing Reed-Solomon method, Hamming method, Cyclic Redundancy Check (CRC), keys combined with various hash functions or a method using a 10-bit value out of the range of application of 8-bit value in 8-10 conversion.

Further, the present invention may be considered to be a growing neural network method, in which, utilizing spherical surface convergence phenomenon, conventionally associated with "curse of dimension", mean distance of samples is calculated with the mean value approximately positioned near the spherical surface, whether a sample is to be assigned to a population or not is determined dependent on whether the probability of a sample belonging to a range defined by the standard deviation thereof is high or not based on statistical probability density function, and assignment in accordance with set theory is established, whereby evaluation function evaluating relevancy of assignment to a population is reconstructed.

Further, the present invention may be regarded as empirical Bayes method or hierarchical Bayes method, that is, an embodiment applied when mean, variance and standard deviation of probability of assignment, probability of appearance or probability of belonging are calculated based on the probability density function of each sample to a population and it is apart by more than three times the standard deviation, that is, more than $3\sigma$. The present invention, however, is different from the simple probability evaluation, as the invention allows classification even when pieces of information are overlapped in a state extremely close to the center of gravity and allows easy quantification, even in a state impossible on probability theory in which the probability is larger than 1 and closer to the center of gravity of the population, as it utilizes distance evaluation based on prior probability, eigen value and Mahalanobis distance in accordance with Bayes identification function. Here, the degree of divergence from a population may be considered to evaluate whether it is in a range based on the mean and standard deviation of the population, in accordance with the probability density function, considering the number of samples and other conditions.

Other distance expression derived from an analysis of covariance matrix structure necessary for Mahalanobis distance, or calculation of distance to a center of gravity in a vector quantization space in accordance with K-means method or Schmitt orthogonal decomposition may be used.

As to the method of calculating distance, not only Mahalanobis distance but also Euclid distance, city-block distance, chess-board distance, octagonal distance, hex distance, Minkowsky distance, similarity or a distance obtained by adding a weight to such distance or any such arbitrary distance measuring method may be used, either the eigen values or eigen vectors may be used, distance may be calculated by arbitrarily changing statistical characteristics by arithmetically changing the value of either one, or eigen value itself or norm or maximum component of eigen vectors may be used for calculating the distance.

Further, an arbitrary method such as Jacobi method, Lanczos method, standard eigen value problem, solution of eigen value calculation, Householder method, Alnordi method, QR composite method, single QR method, double QR method, Gauss-Seidel method or Gauss-Jordan method may be used to derive eigen value or eigen vector.

Further, the plurality of pieces of distance information obtained from the plurality of populations may be regarded as sample vector information, and by obtaining eigen values, eigen vectors and norms of the eigen vectors again, it is possible to derive Mahalanobis distance, or the eigen values or eigen vectors of the plurality of populations may be regarded as sample vectors and the distance may be calculated using information such as the norm, eigen values, eigen vectors, mean, variance and standard deviation. Further, a method may easily be conceived in which, by executing such contents in recursive or hierarchical manner, a structure such as Bayesian network is formed.

For time-sequential information or shape information without any association to population as no population exists before classification, Mahalanobis distance to the input information itself, that is, the recent time-sequential information or different shape information may be evaluated, using indexes such as standard deviation, norm and mean based on eigen vector or eigen value, obtained from past time-sequential information or different shape information, using means for deriving maximum eigen value and maximum eigen vector based on power method or the like.

Further, Mahalanobis distance may be evaluated by indexes such as standard deviation, norm and mean based on eigen vector or eigen value, obtained from recent time-sequential information or different shape information.

A method may be used to form a new population and association to the population may be established, while classifying information based on the standard deviation or mean value of distances evaluated in this manner.

Further, at a conditional branch involved in the distance calculation, values near a boundary may be classified in a probabilistic manner.

Further, the information may not be limited to time-sequential or shape information, and it may include color information, sound information, character information, character code sequence, pronunciation symbol sequence, mnemonic sequence, phonetic symbol sequence, phoneme symbol sequence, phonemic symbol sequence, semantic population symbols, names, shapes, spatial positions, spatial arrangements, pieces of symbols such as phoneme segment symbols or such items, or dynamic variable information such as evaluation variable, feature, symbol value or variation thereof, or static variable information.

Further, the present invention may be used to evaluate and determine input information and to output the result as an artificial intelligence, or the invention may be used for speech recognition to realize voice communication, for image recognition or gesture recognition to operate a device, to execute meaning-based search, or it may be used for internal evaluation of an agent for user interface in an information processing device.

Further, it is possible to find eigen value and eigen vector in recursive manner from the mean and variance of eigen value or eigen vector itself of each population and to derive Mahalanobis distance between populations. Further, it is possible to calculate distance between populations near an orthogonal boundary, by various vector division methods.

In this manner, a plurality of classified populations that are within an arbitrary designated range with each other may be divided, coupled or changed. By way of example, when a distance between mean values of respective ones of a plurality of populations is within 2σ of standard deviation, the populations may be integrated to one.

Further, a method may be possible in which, rather than evaluating the distance from the center of gravity of each population, distance from the center of gravity of a specific population is evaluated, and if the distance is not smaller than 3σ, another population is formed based on the population to which the sample has belonged previously.

Further, a method may be possible in which a sample is assigned to a population to which it had been assigned with high frequency in the past, based on the history of assignment to populations that change as reclassification is performed a number of times. If assignment frequency in the past is almost the same among the populations, the population to which the sample is to be assigned may be determined using a random number.

Further, designation of the range of dispersion may be changed in accordance with the number of reinforcement learning, the center of gravity of a sample to be matched may be used as a reference, or the center of gravity of actually matched samples as a result of match evaluation may be used as a reference, to execute evaluation of reclassification.

Further, the number of populations may not be changed, and only the population to which a sample is assigned may be changed.

Further, a local solution based on likelihood distribution, appearance probability distribution or distance distribution in the population may be regarded as a tentative center, distance to each sample from the tentative center may be calculated, whether the range is statistically significant or not may be discriminated by mean, variance and standard deviation of the obtained distances, and the population or populations may be divided, coupled or changed accordingly.

When a difference between mean vector and sample vector is calculated, whether positive solutions or negative solutions are dominant among solutions resulting from the difference between each element is confirmed, an axis of distance is expanded to positive/negative side, whether the correlation to the center of gravity and mean of the distance information is positive or negative is determined, and how biased is confirmed, to change the classification of populations accordingly.

In addition to the normal distribution described above, chi-square distribution, uniform distribution, normal distribution, logarithmic normal distribution, beta distribution, Cauchy distribution, F distribution, U distribution, t distribution, p variable normal distribution, gamma distribution, logistic distribution, Poisson distribution, Wishart distribution, Hotelling's T2 distribution, power normal distribution, empirical distribution, cumulative distribution function, discrete distribution, binding distribution, bivariate normal distribution, multivariate normal distribution, multivariate exponential distribution, hypergeometric distribution, multidimensional normal distribution, logarithmic series distribution, exponential distribution, half normal distribution, simultaneous distribution, frequency distribution, conditional distribution, marginal distribution, probability distribution, stable distribution, geometric distribution, binomial distribution, negative binomial distribution, Weibull distribution and the like, other distributions including multivariate, multinomial, or multi-dimensional modifications thereof, or test using the same may be used for calculating distance or evaluating assignment, in accordance with the present embodiment.

Further, Gram-Schmidt decomposition, Cholesky decomposition, singular value decomposition, eigen value analysis, matrix, norm, condition number estimation, solution of linear equation or other arbitrary method in accordance with linear algebra approach may be used for calculating distance or evaluating assignment, in accordance with the present embodiment.

Further, correlation coefficient matrix, multi regression analysis, principal component analysis, factor analysis, canonical correlation analysis, multi-dimensional scaling, discriminant analysis, classification tree, log linear model, cluster analysis, dendrogram, minimum spanning tree, or other arbitrary method in accordance with multivariate analysis may be used for calculating distance or evaluating assignment, in accordance with the present embodiment.

Further, least squares regression, non-linear regression, stepwise regression, robust regression, spline approximation, super smoothing, kernel smoothing, generalized linear model, generalized additive model, comparison of models on deviance, Alternating Conditional Expectation (ACE), Additivity and VAriance Stabilization for regression (AVAS), projection pursuit regression, square error median regression, Classification And Regression Trees (CART) or other arbitrary method in accordance with regression analysis may be used for calculating distance or evaluating assignment, in accordance with the present embodiment.

Further, one-way/two-way analysis of variance, Turkey method, Latin square, factorial design, one-way/two-way robust analysis of variance, or modification of these for multidimensional or multi order application may be used for calculating distance or evaluating assignment, in accordance with the present embodiment.

Further, autocorrelation, autoregression (conventional method and robust method), ARIMA (Auto Regressive Integrated Moving Average) model, order selection in accordance with AIC (Akaike's information criterion), vector AR (Auto Regressive) model, arbitrary variable spectrum analysis, Fast Fourier Transform, wavelet transform, Hadamard transform, power transform, Box-Cox power transform, multi-parameter power transform, power normal transformation, Procrustean transformation, z transform, logarithmic transformation, missing value transformation, inverse normal transformation, normal transformation, angular transformation, Laplace transform, logit transform, tests, various filtering techniques such as high-pass/low-pass/band-pass/band-notch filtering using an arbitrary evaluation function, many classical and robust smoothing methods, Lebesgue integral, path integral, oscillatory integral, elliptic integral, high order differential, logarithmic differentiation, partial differentiation, elliptic differential, various functional derivatives, stochastic differential, Lie derivative, Markov differential, Itoh differential, Black-Sholes formula, arbitrary elementary function, arbitrary polynomial function, arbitrary rational function, exponential function, logarithmic function, trigonometric function, hyperbolic function, arbitrary floor or ceiling, gamma function, zeta function, elliptic function, Bessel function, Lambert W function, arbitrary error function, beta function, green function, σ function, Euler's φ function, partition function, Mobius function, L function, Ackermann's function, Dirac delta function, arbitrary heavy side step function, Dirichlet's function, arbitrary one-way function, or other arbitrary method or function in accordance with time-sequential analysis or signal processing may be used for calculating distance, evaluating assignment, or for correcting the same, in accordance with the present embodiment.

Further, Cox's proportional hazard regression, Poisson regression, modified Cox model of Anderson-Gill, Kaplan-Meier method, Fleming-Harrington survival time analysis or other arbitrary method in accordance with survival time analysis may be used for calculating distance or evaluating assignment, in accordance with the present embodiment.

Further, test using Goodman-Kruskal's coefficient, Kruskal-Wallis test, one-sided test, $\chi^2$ test, two-sided test, test of population mean of normal distribution (population variance known), test of population mean of normal distribution (population variance unknown), t-test, test of population variance of normal distribution, test of independence, test of variance, test of mean, runs test, test related to variance-covariance matrix, test of effectiveness of multigroup discrimination, Wilks' lambda statistic test, test of variable contribution to multigroup discrimination, partial Λ statistic test, Acichie-Koul test, Ansari-Bradley test, Cohen's Kappa, Weighted Kappa, Durbin test, Durbin-Watson test, eigen value test (Bartlett), Kolomogorov-Smirnov test, Kolmogorob-Smimov one-sample test, Lepage type test, Lillifores test, logrank test, Ansari-Bradley test, Fisher's exact test, Friedman test, F-test, Hodges-Lehman Estimation, Hotelling's T2 test, Jonckheere test, k×c contingency table (independent) chi-square test, Klotz's normal scores test, Kolmogorov-Smirnov test, Kruskal-Wallis test, test of uniformity of k populations proportion, Mood test, Moses test, Page test, Runs Test, Linear by Linear Association Test, CMH Test for Stratified Data, Logrank Test, Tarone-Ware Test for Trend, Fisher-Freeman-Halton Test, Pearson's Product-Moment Correlation Coefficient, Pearson's Chi-Square Test, Likelihood Radio test, Savage Score Test, Shapro-Wilk Test, Siegal-Tukey test, Tukey's additivity test, Wald test, Watson test, Wilcoxon type test, Wicoxon-Mann-Whitney test, Bartlett test, Yates correction, Mann-Whitney test and various other such sample test, test of relevancy of contingency table, test of independence, test of adaptiveness or other arbitrary method as test methods may be used for calculating distance or evaluating assignment, in accordance with the present embodiment, and the present invention may be regarded as "Bayesian function with appearance probability test" in which distance evaluation function is formed in statistically probabilistic manner and degree of assignment relevancy to the function is tested.

Further, methods described above may arbitrarily be combined and used for calculating distance or evaluating assignment, in accordance with the present embodiment.

Further, an arbitrary coefficient calculating operation may be executed, in which one having shorter distance before normalization using standard deviation is given priority at the time of classification.

Further, in accordance with normalized distances for a plurality of populations calculated during the operation, the population to which the sample is to be assigned may be recognized or evaluated.

Further, by connecting a plurality of evaluation results in the form of a network, and using normal distribution as the weight of connection, evaluation function having an arbitrary network structure may be formed.

Further, the invention may be applied to EM algorithm or K-means, and by a combination of arbitrary methods such as evaluating whether the belonging sample is within 3σ or not, evaluating relevancy of classification, and executing an optimal clustering, it may be utilized for improving performance of an arbitrary clustering process.

Further, factor axis rotation or analysis, factor analysis method, multivariate analysis method or cluster analysis method such as Kaplan-Meier method, varimax method, quartimax method, union intersection method, quartimin method, biquartimax method, promax method, oblimax method, oblimin method, orthomax method, Ward method, equamax method, Kaplan-Meier method, Kaiser-Dickman method, Gauss-Doolittle method, covarimin method, oblique rotation method, successive factor general varimax method, centroid method, method using studentized residuals, Beaton's method, nearest neighbor method, furthest neighbor method, group average method, median method, Ward method, flexible method and the like may be used for optimizing eigen vector or eigen value space, for evaluating distance, or used as evaluation function for evaluating distance.

Further, Ansari-Bradley score, Klotz's normal score, Savage score, Siegel-Tukey score, signed normal score, van der Waerden's normal score, Mood score or other scoring method may be used for scoring feature or scoring function output result, thereby to form an evaluation function, to evaluate output of an evaluation function, or to score again the result of evaluation.

As described above, by combining known functions, statistics methods, scoring methods, classification methods, test methods, optimization methods and statistical approaches, various applications, improvement of performance, improvement of function or the like readily becomes possible.

Next, an information processing system for offering various services will be described.

By way of example, the present invention may be used for classifying variables and attitude names for realizing an operation in an operation learning, based on association of information for an operating machine such as a robot. In this connection, an information processing system offering remote robot control service in which only the attitude name is transmitted to an apparatus such as a robot through a communication line, operation of remote dance service or the like of the robot is analytically processed and re-used, or an operation control system or service based on feature learning of operation and/or control method of an apparatus including an arbitrary driving function may be possible, and using such system, a machining robot, a sorting robot, a conveying robot, a nursing-care robot, a pet robot, a helper robot, an interactive robot, a home-care robot, an agricultural robot or the like may be formed.

By way of example, assume that the present invention is applied to robot concept, behavior or determination. Here, energy obtained by the behavior of the robot may be classified to "excessive, moderate, equilibrium, attenuating, lost" based on the consumed energy, taken energy, or user preference assessment. In association with such classification, features such as sensor input values or analyzed values related to ambient image, sound, temperature, moisture, air composition, smell, liquid/material composition, taste, weight, acceleration, shock or pressure, secondary features based on the state of transition of features, tertiary features based on the state of transition of secondary features, and higher order features of multi-dimensional combination of such features may be collected and classified using the present invention. Here, analogue transition between each of the afore-mentioned 5 categories may be possible, or the categories may be further classified to form an evaluation function, or the classification may be represented by negative/positive value or values of one or an arbitrary number of variables.

Consider methods of forming various evaluation functions related to concept, behavior and determination of a robot. A method may be possible in which, when one such variable is used and the variable is near 0 or when a plurality of such variables are used and their values represent an equilibrium, and when information of a procedure by which energy was obtained in past classification or information of a procedure classified as the procedure for reducing cost to obtain preference assessment by the user or energy is at a close distance to the input feature, that is, the information of procedure successful at obtaining the energy, interest variable of the robot may be increased/decreased, when energy acquisition is excessive or the apparatus may be damaged accordingly or when energy is lost and ability to move lowers accordingly, fearfulness variable may be increased/decreased, or when the energy attenuates considerably as the energy is acquired, boredom variable may be increased/decreased. Here, the information of procedure may be provided by recording time-sequential change of the behavior of the apparatus itself.

Further, considering methods of forming various evaluation functions related to concept, behavior and determination of a robot, even when acquired energy or preference assessment by the user is smaller than the attenuating energy, if there is information of any procedure by which larger energy is available by combining a plurality of such elements, a procedure by which it is expected from the past classification that energy provided by other apparatus or living organism or preference assessment by the user in the future would be large, or a procedure that is expected to avoid damage to an apparatus of the same type, the behavior of the apparatus may be controlled based on such a procedure. By way of example, a device used for a pointing device such as a capacitance sensor pad may be used to evaluate user's hitting or touching, and a hit may be evaluated as a negative evaluation and a pat may be evaluated as a positive evaluation. Alternatively, a method may be possible in which when the user reacts to an utterance of a robot, it may be regarded as a positive evaluation, and no reaction may be regarded as a negative evaluation, and such information may be classified using the method of the present invention.

Further, considering methods of forming various evaluation functions related to concept, behavior and determination of a robot, utilizing the classification in accordance with the present invention, when slow consumption of energy is recognized for a long period exceeding an arbitrarily defined time period and no specific instruction is given by the user, a so-called standby mode or sleep mode as used in connection with a personal computer may be entered automatically to prevent reduction of energy, or operations instructed in the past but pending may be executed.

Further, considering methods of forming various evaluation functions related to concept, behavior and determination of a robot, it may be used for a method in which the interest variable increases/decreases when a sample does not belong to any population classified in the past, when a new center of gravity of a population appears or when there is information that belongs to the classified population and provided profit to others, the boredom variable increases/decreases when it is extremely closer to a center of gravity of a population classified in the past, or the fearfulness variable increases/decreases when extreme energy attenuation or loss, loss of credibility or negative evaluation by the user, or damage to the apparatus occurs because of the result of determination of the population classified based on the past determination, or it may be used for processing means utilizing such classification information.

Further, considering methods of forming various evaluation functions related to concept, behavior and determination of a robot, these names, that is, interest, fearfulness or boredom may have different names as variables representing psychological states such as curiosity, fear or weariness. By classifying behaviors that have been positively evaluated or negatively evaluated by the user, whether an arbitrary process or behavior may be acceptable or not may be classified, learned or suppressed. Discrimination of oneself and others may be determined through probabilistic evaluation of a range that is influenced by a change in attitude state, energy state or positional state of oneself accompanying an active behavior. Evaluation as to whether the behavior is active or not may be realized through probabilistic evaluation as to whether it is in synchronization with a spontaneous signal based on a change in energy state of oneself. When an antipathy variable or fearfulness variable increases/decreases, or when energy or positive evaluation is not acquired as expected, a variable that represents a stress or suppression may be increased/decreased.

Further, information processing system may be possible that offers psychoanalysis service or fortune telling service, based on association of names recalled by a user and used for human subjective evaluation analysis or psychoanalysis, objective information such as operations, behaviors, age or birthday of a user, character, emotion or affection information of the user and the name information of expected result or state, personnel evaluation service in which operation name, personnel name, operation difficulty and operation achievement are associated to each other, contents analysis service, or services oriented to individual preference reflecting user tastes or popularity of goods or services, by classifying information and extracting tendency based on labels as individual items and features as their variables, using statistical variable information such as a questionnaire, related to names representing elements of one's hobby.

Further, it may be used for classification or recognition of natural information based on indexes such as living organisms, geography, geologic condition names, positions, size, colors, shapes, compositions, materials, components or states, or information processing service offering environmental research service may be possible, based on analysis based on information association. By way of example, an information processing system may be possible in which indexes are regarded as nodes of an assumed network model, distance from a certain index to another index or human is used as positional and/or temporal co-occurrence relation or co-occurrence probability of other index or information involved therebetween, and anteroposterior relation or number of indexes is used as semantic state, to analyze, build or propose a natural state. Here, concept of the relation between nodes and links may be arbitrarily changed as frequently observed in a network model such as HMM.

Further, an information processing system may be possible that offers security management service, based on association of information utilized for crime prevention device by statistically classifying human behavior near a building, or utilized for tracking frequent violators using an image-pickup device on the road or an alarm device. By way of example, the buildings, goods and humans may be regarded as nodes of an assumed network model, distance from a certain building or goods to a certain person is used as positional and/or temporal co-occurrence relation or co-occurrence probability of the objects or number of people involved therebetween, and anteroposterior relation is used as semantic state, to analyze, build or propose state of propriety or use. Here, concept of the relation between nodes and links may be arbitrarily changed as frequently observed in a network model such as HMM. Further, image features, frequency of appearance, staying time and crime rate may be used as features and states recognized by a human being may be used as labels, and these may be the indexes for classification and evaluation, so that it may be applied to monitoring facility. An "electronic scarecrow" may be possible, which monitors agricultural commodity, or wild dumping, evaluating behavior of animals and the like.

Further, it may be used for analysis based on probabilistic supposition such as chemical analysis or DNA (Deoxyribonucleic Acid) analysis, or information processing system offering medical or chemical service including pharmaceutical preparation or DNA test based on association of information. Here, scientific features such as values of experiments and their names may be used as labels, that is, indexes for classification, or classification base such as physical position where DNA was sampled or affected region and/or age, sex, character, or names of fields of interest such as preferences of hobby, sports, music, movies, political activities and the like may be used as labels for classification, and used for analyzing, designing, or proposing one's life and constitutional tendency, effects of medicine and medical treatment.

Further, an information processing system may be possible that performs engineering analysis for statistically analyzing and labeling engineering characteristics, such as defect detection, earthquake resistance analysis and strength analysis involved in design.

Further, it may be used when an adaptive filter is formed, in filtering for communication equipment, or an information processing system may be possible that offers communication service or information transmitting service, in which a communication base station based on information association in accordance with the present invention is formed for analyzing, building or proposing safe communication path or reliable communication, that provides firewall service, provides spam mail filer, specifies or forms a network connection path, or is used for a method of re-constructing an ad-hoc network in accordance with communication quality such as radio wave intensity or number of connection retrials. By controlling communication based on a result of evaluation of features indicating passage of a specific network path, such as transmitter's name, IP address, a domain, a specific domain or IP space, it may be possible to filter unauthorized spams.

Further, it may be used for estimating states of an affected region, utilizing nouns such as disease name, physical position, condition or chemical material related to medical treatment as labels, and utilizing analysis of shape or condition of the affected portion by a medical device, coefficients or variables obtained through chemical analysis, analysis values or values obtained by processing thereof as features of the sample vector. Alternatively, an information processing system is possible that offers communication-based medical service based on association of information, in which interactive patterns are used as variables for the sample vector, pieces of information are collected and recorded, and counseling is done.

Further, as an internal medical application, an information processing system may be possible, in which relation between human DNA, physical characteristics, blood pressure, body temperature, pulse, biologic fluid or other medical characteristics and disease is regarded as nodes or links as used in a network model, a distance from a certain feature to a certain feature or to a disease is used for weighting evaluation, with the number of medical features or number of diseases covered therein used as feature based on the number of network hops, so that co-occurrence relation or co-occurrence probability of information in the scope of medical field such as wider medical concept, may be regarded as semantic state network of medical features, for performing phatomorphical analysis or proposal for improvement. Here, concept of the relation between nodes and links may be arbitrarily changed as frequently observed in a network model such as HMM.

Further, as a surgical application, an information processing system may be possible, in which relation between bodily disorder characteristics and physical space model, such as human physical portion or physical characteristic and geology or road conditions allowing human movement is regarded as nodes or links as used in a network model, a distance from a certain feature to a certain feature or to the physical space model may be used for weighting evaluation, with medical feature or physical space model covered therein as features, so that co-occurrence relation or co-occurrence probability in the scope of the information field may be regarded as surgical physical function, for offering analysis of physical function disorder or proposal for improvement. Here, concept of the relation between nodes and links may be arbitrarily changed as frequently observed in a network model such as HMM.

According to a general interpretation of the applications described above, names related to special knowledge are used as labels, and correlation between the labels are represented by distance, whereby layer structure of absolute or concrete concept is analyzed, and using a coefficient or variable thereof as a sample vector, classification in accordance with the present embodiment is executed.

In this method, labels related to knowledge names such as various technical terms, persons, places and the like are regarded as nodes and a network structure is formed, hop numbers that corresponds to the node numbers between pieces of information is regarded as the distance, the distance may be used as a feature, or a path finding technique in a communication protocol may be used to find distance between pieces of information in a semantic space, or to evaluate distance. Here, it is also possible to designate a weight at each node as an amount of attenuation for a connection to another node, or a method is also possible in which discrete values of hop numbers are interpreted as continuous amount, for evaluating distance.

By realizing association of information based on hierarchical memory considering such network structure, an information processing system may be possible that offers information providing service or education service in accordance with associative expert service based on classification by the present invention, information distributing service, simulation service predicting effect of element combination such as personnel, material, chemicals, equipment and distribution path, information predicting service including weather forecast, stock price and market rates prediction, earthquake prediction, economic prediction, commodity price prediction, competition prediction, horse racing prediction, and information summarizing service that summarizes newspaper articles, or magazine or book articles.

Further, when information related to a plurality of regions of different languages is classified for persons speaking a specific language by using, as sample vectors, words uttered in accordance with shapes or words uttered accompanying shapes, in accordance with the present embodiment, to effect semantic space classification, an information processing system may be possible using a portable telephone, PDA or communication base station, offering travel guide or translation service, realizing similar services in regions using different languages, based on association of information.

Further, in an interactive user interface, when feature of a word of ambiguous meaning based on utterance probability is used as a sample vector and the habit of the speaker is learned in accordance with the present embodiment, an information processing system may be possible that offers interactive service based on association of information realizing ambiguous interaction.

Further, in a game or the like, when information having conversation models classified and registered for characters is used, it becomes possible to offer a service that enables conversation creating humane atmosphere in the form of a gesture during calculation of distance evaluation, or creating animal-like, plant-like or humane behavior or act by using features obtained by analyzing behavior of animals, plants or people. Further, an information processing system that offers such service is also possible.

Further, an information processing system may be possible, in which credit records and evaluation values are used as sample vectors, and evaluation distance in or between organizations is calculated for classification and reliability distance among evaluators is obtained, whereby levels of dividend, achievement evaluation or performance evaluation is determined, money payment structure or credit line is set, discount systems, profit return method, ballot casting method, research method, or price determination or evaluation for determining price of product or dividend is executed.

Further, an information processing system may be possible in which information is collected based on map and region, and by way of example, information such as sound feature representing position and name, image feature, temperature feature, weather feature, population density or the like is used as sample vector, and an appropriate name is allocated as a label for classification, whereby location-based information support is offered. An information processing system may be possible, in which densely populated regions such as towns or villages are regarded as nodes or links as used in a network model, and distance from a certain location to another location is used as a feature for weighting, with the number of locations covered therebetween regarded as the number of network hops, so that co-occurrence relation or co-occurrence probability, or positional relation between locations in the scope of the regional name field such as city, county, or state, of wider information including number of towns, population, production output, traffic amount, economical scale, management numbers thereof, temporal and/or physical positional relation, is used as semantic state, for offering analysis, construction or proposal of the manner of moving, utilizing car navigation or the like.

Further, using conventionally known information for grasping situation as features, state of distribution of products may be analyzed using ID tags or the like, state of vehicle passage may be analyzed, or state of human movement may be analyzed, to build index information for managing distribution state, whereby an information providing service providing detour information or traffic jam information may be realized.

Further, an information processing system may be possible in which information objectively representing human communication such as time of co-existence of people, joint authorship information, family registration, collaborator information, the number of pieces of such information and/or frequency of appearance may be regarded as sample vectors or as nodes or links as used in a network model, and distance from a certain person to another person is used as a feature for weighting with the number of people covered therebetween as the number of network hops, for offering communication analysis or proposal of human relations, using number of people, number of participating groups, management numbers thereof, temporal or physical positional relation, the number of communication among people or number of viewing as the state of communication.

Further, an information processing system may be possible in which words related to information based on a certain language and information based on a different language or arbitrary information are associated, whereby classification or evaluation reference for offering services available between different languages is formed. A service performing automatic correction of documents with high accuracy may be possible, using error in writing, omissions, erroneous interpretation designated by a reader of sentences prepared by character recognition, manual input or speech recognition.

Further, an information processing system may be possible, in which video information or audio information based on location and words or arbitrary information related to the video or audio object are associated, whereby classification or evaluation reference is formed for offering location based service. An information processing system may be possible in which words are regarded as nodes or links as used in a network model, and distance from a certain word to another word is used as a feature for weighting with the number of words covered therebetween as the number of network hops, so that co-occurrence relation or co-occurrence probability of information, the number of characters or the number of words, management information, preceding/succeeding relation of words based on temporal positional relation is used as semantic state, for offering analysis, construction or proposal of semantic relation.

Further, it is also possible, by using eigen value or eigen vector to evaluate shape information of a two-dimensional or three-dimensional shape based on image information, motion information or coordinate information groups, and based on similarity defined by the evaluation distance, to evaluate the state of infringement of intellectual property, related to design infringement or copyright infringement. Here, considering information-to-information distance of the population to which the sample belongs and the information as the object of evaluation, that is, the sample, or considering states of release of similar shapes along with time-sequential variation from the time of release of the product sample, the information-to-information distance may be evaluated to quantify state of obsolescence or similarity.

Further, an information processing system for selecting arbitrary information, product or service may be possible. Further, an information processing system may be possible that selects arbitrary information, product or service by analyzing relation between music and words recalled in association with the music, and statistically classifying related information.

Further, an information processing system may be possible that selects arbitrary information, product or service by analyzing relation between costumes, clothing or accessories and words recalled in association with the costumes, clothing or accessories, and statistically classifying related information.

Further, an information processing system may be possible that selects arbitrary information, product or service by analyzing relation between tactile impression and words recalled in association with the tactile impression and statistically classifying related information.

Further, an information processing system may be possible that selects arbitrary information, product or service by analyzing relation between taste and words recalled in association with the taste and statistically classifying related information.

Further, an information processing system may be possible that selects arbitrary information, product or service by analyzing relation between smell and words recalled in association with the smell and statistically classifying related information.

Further, an information processing system may be possible that selects arbitrary information, product or service by analyzing relation between weather and words recalled in association with the weather and statistically classifying related information.

Further, an information processing system may be possible that selects arbitrary information, product or service by analyzing relation between video image and words recalled in association with the video image and statistically classifying related information.

Further, an information processing system may be possible that selects arbitrary information, product or service by establishing relation among pieces of information obtained from sensory organs and words such that pieces of information of different types, for example, words related to taste and costumes or words related to smell and accessories, are related to each other. An information processing system may be possible in which words are regarded as nodes or links as used in a network model, and distance from a certain word to another word is used as a feature for weighting, with the number of words covered therebetween used as the number of network hops, so that co-occurrence relation or co-occurrence probability of information, the number of characters or the number of words, management number, preceding/succeeding relation of words based on temporal positional relation is used as semantic state, for offering analysis, construction or proposal of semantic relation. Here, concept of the relation between nodes and links may be arbitrarily changed as frequently observed in a network model such as HMM.

Further, an information processing system may be possible that provides arbitrary information, product or service based on a word related to sensitivity recalled in association with each item.

Further, from words that are recalled in association, nonverbal symbols or classification codes, such as character codes classifying adjectives or adverbs, sensation codes classifying sensations, sensitivity codes classifying sensitivities, feeling codes classifying feelings, subjectivity codes classifying subjectivity, or shape code numbers classifying visual shapes may be formed, and relation may be established between the codes and other arbitrary pieces of information, or relation may be established between a plurality of pieces of arbitrary information, such as features and recognized symbols using such codes, whereby a method of defining co-occurrence matrix or co-occurrence distance in accordance with the number of characters or the number of words, management number, preceding/succeeding relation based on temporal positional relation is formed. An information processing system may be possible that has a concept dictionary or concept index formed by using these, recorded in a storage medium.

In this manner, by establishing relation between arbitrary pieces of information, by applying methods of information selection, information distribution, information provision, information extraction, information processing, information analysis, information prediction, information transmission, information classification, information separation, information translation, information conversion, information summary, information search, information comparison, information evaluation or information research, an information processing system may be formed that provides or supports arbitrary information, arbitrary product or arbitrary service.

More specifically, using an arbitrary feature, a group of sample information of information necessary for the above-described information processing system examples is generated. The samples may be speech or music, picture or photograph, movie, chemical component stimulating gustatory sense or sense of smell, sensory temperature or touch, information such as measurable length, weight, speed or position, frequency of appearance or co-occurrence probability of words when considering sentences, appeared character frequency as characteristic of the sentence, features formed by representing arbitrary target pieces of information in combination, or combination or processing thereof, or composition ratio of such features.

Here, arbitrary ID (Identification Data), labels or codes for such information or features may be manually designated for classified populations at the initial stage, or classified previously based on mean and variance of all the groups of sample information utilizing the present embodiment.

Sample information classified with arbitrary variable or coefficient in this manner is repeatedly subjected to recursive classification in accordance with the present embodiment until the number of populations becomes stable, and labels, IDs, codes, classification numbers, serial numbers, management numbers obtained as a result of execution until the number of population becomes stable are again used as specific labels, IDs, codes, classification numbers, serial numbers, management numbers based on human subjectivity or in accordance with an arbitrary method of information processing. The labels, IDs, codes, classification numbers, serial numbers, management numbers may be used as a search key of a database, or it may be used as an attribute of a file in a file system.

As a result, the sample information has the relation between the obtained labels, IDs, codes, classification numbers, serial numbers, management numbers and names used by people associated with arbitrary features such as result of matching or path search based on applications including co-occurrence matrix, uni-gram, bi-gram, N-gram, composite N-gram, CDP matching of arbitrary stage or arbitrary dimension not limited to two-dimension or three-dimension, DP matching, Viterbi search, N-best method, trellis method or the like, in accordance with index processing method such as binary tree or hash buffer, and thereafter efficiently forms a concept dictionary or concept index classified and recorded in accordance with the present invention. Then, using a database constructed by a recording medium using the information classified and generated in accordance with the present invention as an index or evaluation parameter, information input by a person is associated with an appropriate label, ID, code, classification number, serial number or management number, information related to the label, ID, code, classification number, serial number or management number is searched for, and intended information, service, product, means, procedure, path or time schedule may be presented or proposed for the user, or offered as information providing service in accordance with various purposes of the user, or classified and recorded on a recording medium in accordance with the purposes.

In this manner, an information processing system for the above-described various information providing services is realized, by establishing relation between information input by a user and an arbitrary information based on the reference classified in accordance with the present embodiment, or evaluating relevancy thereof. It is possible to realize services considering intensions, preferences, background or situation, through these applications.

Further, as to the information representing variation or state of co-existence of information such as co-occurrence matrix, co-occurrence probability or probability transition matrix in numerical values as described in the present embodiment, items smaller than a prescribed threshold may be removed from the objects of evaluation, pieces of information at positions further than a prescribed distance from the mean, based on standard deviation calculated from variance of all probabilities, may be removed from the objects of evaluation, the number of evaluation dimensions may be degenerated by Gaussian elimination, or items for evaluation may be added under similar conditions.

In addition, the pieces of information numerically representing state of co-existence of information such as occurrence matrix, co-occurrence probability or probability transition matrix, may be classified into an information group that improves performance, is effective or meaningful and is positively evaluated by human subjectivity, an information group that degrades or decreases effects and is negatively evaluated, an information group of which change is not subjectively recognized, and an information group that is a taboo, as co-occurrence thereof causes significantly deteriorated result, whereby efficiency of use in execution can be improved. Though there are four categories for the classification here, a larger number of categories may be used in accordance with actual use.

Further, information classifying device 100 may include an external storage device for recording data on a recording medium. The recording medium includes recording medium such as a flash memory, CD-ROM (Compact Disk Read Only Memory), a hard disk or a floppy (registered trademark) disk, on which a program, script or source code for executing the procedure on the information processing device is recorded as information.

Further, information classifying device 100 may be provided with a transmitting/receiving device serving as both wired/wireless communication means or bus-connecting means such as Ethernet (registered trademark), modem for portable telephone or wireless LAN (Local Area Network), an arbitrary input device or sensor such as an image pick-up device or a sound capturing device, an inclination sensor, an acoustic sensor, an optical sensor, a direction sensor, a GPS, a temperature sensor, a moisture sensor, a geomagnetic sensor, a keyboard, a mouse, a tablet or a scanner, a display device such as a two-dimensional or three-dimensional display, a sound production device such as a speaker, a device or manufacturing apparatus for composing material using an arbitrary drug or chemical material, a device for printing or print-making, or an arbitrary output device such as a robotic arm or a wheel, or it may be provided with an optical terminal and/or electric or electromagnetic terminal or the like for inputting/outputting arbitrary signals to/from such device or devices. Further, such components may be provided inside or outside the device.

Further, an information terminal or information processing device such as a personal computer, car navigator, a core server or a communication base station, or a portable terminal such as a portable telephone, a wrist watch, an accessory terminal, a remote controller, a PDA, an IC card, an intelligent RFID, a terminal embedded in a body or the like including the information classifying device 100 may be possible, and as the present invention is an application of algorithm execution, it can be implemented on an arbitrary device provided that an operating circuitry is mounted.

Further, a control device controlling a mechanical device with a driving system such as a robot, an electric train, a ship, an airplane, a vehicle, a bicycle, a special purpose vehicle, a machine tool, an artificial satellite, vending equipment, communication equipment, conveying equipment, processing facility, air-conditioning facility, waterworks, electric power equipment, gas equipment, sanitary equipment, agricultural equipment, ocean facility, construction equipment, monitoring equipment, accounting equipment, housing equipment, entertainment facilities, safety equipment, traffic equipment, power equipment, educational facilities, production facilities or a micro machine may include the information classifying device 100.

Information classifying device 100 may be reduced to a portable size, and it may be used as an information terminal.

Further, information classifying device 100 may be an information processing device having a function of improving social convenience by connecting and exchanging communication among a plurality of different users with charges on communication imposed in some cases.

Though information classifying device 100 has been described in the present embodiment, it is not limiting, and the present invention may be realized as an information classifying method causing a computer to execute the process described with reference to FIG. 2, or an information classifying program causing a computer to execute the process described with reference to FIG. 2.

Figure 6:
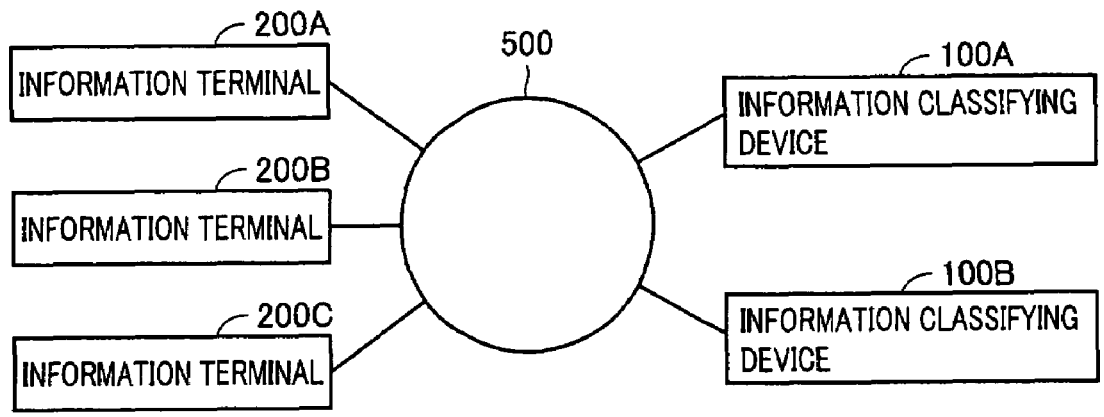
FIG. 6 schematically shows the information classifying system in accordance with an embodiment of the embodiment.

FIG. 6 schematically shows the information classifying system in accordance with a modification of the present embodiment.

Referring to FIG. 6, the information classifying system includes information processing devices 100A and 100B, and information terminals 200A to 200C. Information processing devices 100A and 100B and information terminals 200A to 200C are connected to each other through a network 500 such as the Internet or a telephone network.

Information processing deices 100A and 100B each have the same functions as information classifying device 100 described above. Either one of information processing devices 100A and 100B classifies pieces of sample information as the object of classification to a plurality of populations in response to a request from any of information terminals 200A to 200C, and transmits the result of classification to the information terminal that issued the request.

By way of example, either information processing device 100A or 100B receives a plurality of populations from any of information processing terminals 200A to 200C, reclassifies pieces of sample information belonging to the populations, and transmits the classified populations to the information terminal that made the request. In this manner, populations to which pieces of sample information are classified in an autonomous and stable manner can be provided.

Further, the invention may be applied to an information providing system providing ASP (Application Service Provider) type service, including information processing devices 100A and 100B and information terminals 200A to 200C such as described above, may be implemented as a database device, may be implemented as a recording medium recording the classification service in accordance with the present invention incorporated in the database device for providing a service, or may be implemented as an information distributing device using the classification based on the present invention, using a communication line.

Further, either information processing device 100A or 100B may receive sample information as the object of classification from any of information terminals 200A to 200C, determine to which population among the populations stored in a storage of the information processing device the information is to be assigned, and transmit the information identifying the determined population to the information terminal that made the request. In this manner, information identifying the population to which the sample information as the object of classification is to be assigned can be provided in an autonomous and stable manner. Further, a charge may be imposed on the information terminal that made the request.

Further, the information formed in accordance with the present embodiment may be recorded on a recording medium and distributed as it is, distributed appended to a book, or distributed using communication environment. Here, recording medium such as a CD-ROM or a DVD-ROM (Digital Versatile Disk Read Only Memory), a printing medium such as two-dimensional bar-codes, an electronic medium such as a flash memory, or a recording medium on which storage is done over a distance through a telephone line, ADSL (Asymmetric Digital Subscriber Line), an optical fiber or the like may be available.

Further, the present invention may be configured as a data base searching system in which any of information processing devices 100, 100A and 100B of the present embodiment includes, in addition to the components described above, a database for storing classified populations, finds to which population the sample information as the object of classification received from the user or from any of information terminals 200A to 200C belongs, and passes the result of finding to the user or to any of the information terminals 200A to 200C. Further, the present invention may be implemented as a database constructing device constructing such a database.

In connection with the contents of the database described above, they may be reclassified by evaluating degree of assignment relevancy of each sample to respective populations, based on the distance from the center of gravity of the population to which it belongs or other population, obtained by distance calculation in accordance with a distance evaluation function as the distance evaluating method using the present invention, and arbitrary information to be provided to the user to realize a service, such as classification information including a table, records or indexes as a reference to be presented to the user or classification reference, expression information, and queries or keywords issued in connection therewith, may be updated and/or changed, or optimized, to realize highly convenient service.

Further, for a search, as is conventionally and generally used, when arbitrary IDs/labels match each other, or when an object of which evaluation distance in accordance with an arbitrary method of distance evaluation using the classification method of the present invention as an index, is evaluated as close to arbitrary features with each other associated with arbitrary IDs/labels with each other, the object is determined to belong to a similar field/class, and selected and presented to the user as the search result.

Further, by using the evaluation and classifying method or the result of classification in accordance with the present invention for the valid/invalid flag or flag item of a genetic algorithm, a classification evaluation function applicable to a state in which arbitrary feature or pieces of information are related in a probabilistic manner may be realized, and a flexible method of classification may be realized by changing combination of valid functions depending on the situation.

In accordance with the database forming device described above, a device offering an arbitrary service may be realized, by classifying and searching pieces of information of which tendency analysis has been conventionally difficult such as customer preference, tendency of nature information, economical trend, tendency of animal behavior or human psychological tendency, using a database characterized in that items of IDs, variables, tables, records and indexes as well as contents classified by the present invention are stored.

Further, information classifying device 100 in accordance with the present embodiment may be considered as follows.

Information classifying device 100 constitutes a distance calculating unit that calculates a distance between k samples $a_k$ belonging to a certain population A to the population A. A distance $D_k$ is calculated by the distance calculating unit, and from the values obtained by using the statistical information calculating unit such as calculated distance of each sample $a_k$ to the population A, the mean distance value $\mu_a$ between population A and sample $a_k$ and standard deviation $\sigma_a$, degree of assignment relevancy to the population is evaluated, based on appearance probability in statistical normal distribution.

When the distance between the sample $a_k$ and the mean distance value $\mu_a$ is larger than $3\sigma_a$ (three-times the standard deviation), which is the value representing probability of 99.7% of appearance in accordance with normal distribution with the mean being the center, the degree of assignment relevancy evaluating unit assigns the sample to a different, closer population B or population C, or to a new population, and otherwise, maintains the sample belonged to population A as before, and in this manner, recursive classification is done such that the group of samples belonging to population A form a normal distribution.

Figure 7:
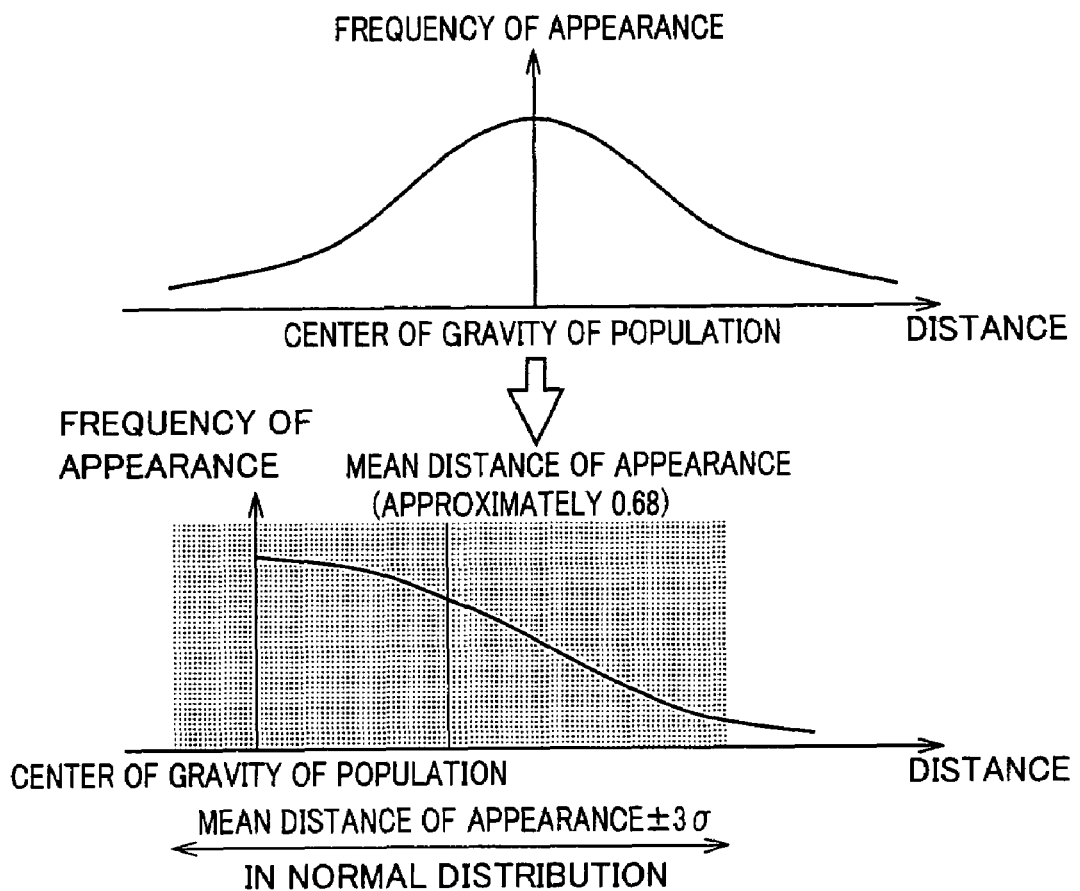
FIG. 7 shows an example of normal distribution.

When normal distribution such as shown in FIG. 7 is realized, the distribution is symmetrical, and when distance to the center of gravity is considered, the mean distance from the population is positioned approximately at 0.68σ, and not lower than 99% of samples of the population are covered in the range of 3σ. A human-prepared population, however, has vague boundary, and asymmetric distribution such as described with reference to FIG. 8 often results.

Figure 8:
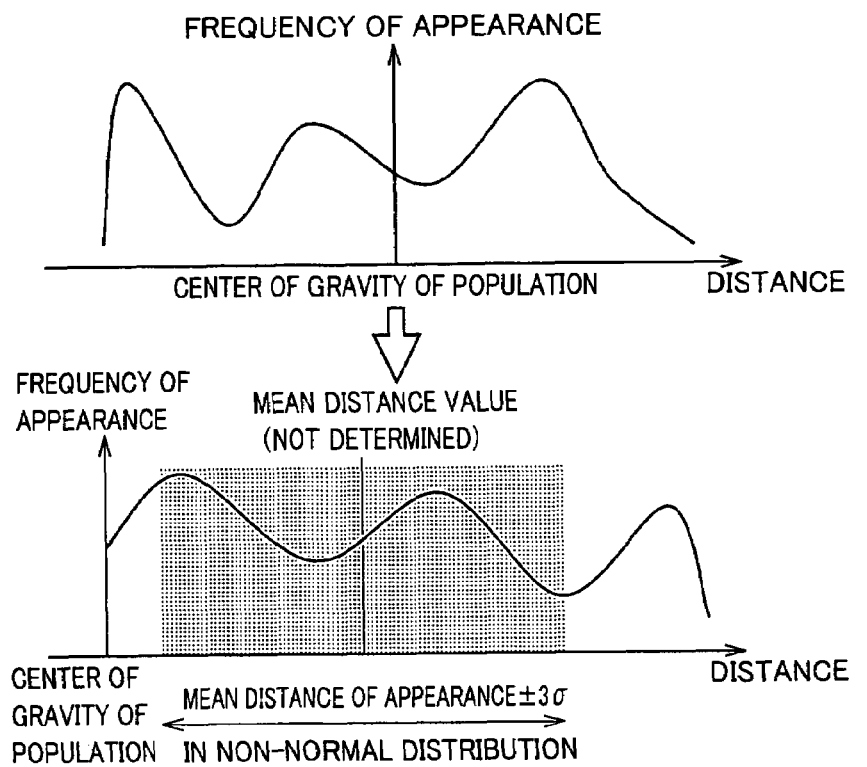
FIG. 8 shows an example of non-normal distribution.

Therefore, in a non-normal distribution such as described with reference to FIG. 8, the mean position is not constant, as it depends on the situation of samples, and hence, it is not always certain whether 99% or more samples from the center of gravity of the population are covered within 3σ from the mean distance value.

Therefore, in the present embodiment, from the contents described above, when there is a sample of which distance from the center of gravity of the population is outside the range of 3σ from the mean distance value as shown in FIG. 3, the sample is assigned to a population, if any, that covers the sample in the 3σ range, and if the sample is not covered in the range of 3σ of any population, a new population C is formed. Here, if there is any statistical problem arises, for example, if the number of elements of population C is smaller than the necessary number of evaluation dimension, the new population may not necessarily be used for evaluation.

In this manner, relevance of information boundary obtained deductively based on human designation is confirmed inductively by a statistical method based on the probability of appearance in the normal distribution of the distance from the center of gravity. If it is determined to be irrelevant both deductively and inductively, a population is tentatively formed, and if the population has relevant center of gravity, it remains through subsequent continuous deduction and induction, and if it is irrelevant, it is culled out, so that only the population having appropriate centers of gravity are left eventually.

As a result, division, combination or change of population or populations is done based on the normalized vector-to-vector distance obtained by normalizing distance information between each element and each population, and therefore, statistical normal distribution can be expected on solid base. Thus, an information classifying device performing information classification approximating normal distribution as much as possible can be provided.

When centers of gravity of populations are extremely close, for example, when there are populations at a distance within the range of 1σ from each other, the populations may be integrated, to prevent inadvertent increase of populations. As a matter of statistical convenience, under conditions that require statistical considerations, as in the case if sufficient samples cannot be collected, or if a sample or population as the object of evaluation is further by 4σ or more, viewed from the standard deviation and mean obtained from a group of samples obtained by integrating a plurality of populations in the neighborhood of about 5σ from a specific population or from overall samples, such a population may be removed.

Therefore, it becomes possible to realize classification of information such as abstract concept or vague expression, sensitivity information and the like based on human sense that have been difficult to classify through quantification, and hence, human-friendly service, or a device, information processing system, a communication base station or portable terminal realizing such service can be provided. Therefore, it is possible to use the present invention as an index for executing RSS (RDF Site Summary) or the like on a portal site of the Internet, a search site, a shop site, an SNS (Social Networking Site), an expert system site for sharing knowledge, an auction site, a screening system for classifying information, an authentication site handling credit information or authentication information on a network, aggregate service, tangible interface or graphical interface of an information processing device, agent interface, robot, virtual reality or augmented reality. Further, the present invention may be used as a classification index for meta expression format such as XML (eXtensible Markup Language), SOA (Service Oriented Architecture), SML (Simpler (or Stupid or Software) Markup Language), MCF (Meta Contents Framework), DTD (Document Type Definition), GML (Geography Markup Language), SMIL (Synchronized Multimedia Integration Language), SGML (Standard Generalized Mark-up Language), RDF (Recourse Description Framework) or the like. Further, a service may be offered by arbitrarily combining various protocols or scripts, or information processing languages such as SOAP (Simple Object Access Protocol), UDDI (Universal Description, Discovery, and Integration), WDL (Web Services Description Language), SVG (Scalable Vector Graphics), HTML (Hyper Text Markup Language) and the like.

[Modification]

Next, a modification of the present embodiment will be described. By way of example, assume that the sample for evaluation $$\vec{X} \qquad \text{[Expression 24]}$$

includes elements $\{x1, x2, x3, x4, x5, x6, x7, x8\}$, and an input vector of the evaluation function $$\vec{Y} \qquad \text{[Expression 25]}$$

includes elements $\{y1, y2, y3, y4, y5, y6\}$. An identifier such as a name or an element ID is given beforehand to each vector element.

As for the name or element ID as the identifier of the element, viewed, for example, from the point of speech recognition, it may be a label having one meaning as in the case of a phoneme. Alternatively, an arbitrary, efficient representation may be given as an identifier representing state of transition of phonemes, by combining higher and lower concepts of abstract labels such as a phoneme and phoneme segment. As to the higher and lower concepts, concepts used in information space of an arbitrary field such as video elements, products, art, culture, movies, music and the like may be used, whereby applications suitable for respective fields can be realized.

At the time of distance evaluation, sometimes the samples and the names or element IDs as labels or identifiers given to the evaluation function are the same, and sometimes they are not the same or switched, as shown below.

TABLE 1

| sample vector $\vec{X}$ | evaluation function input vector $\vec{Y}$ |
|---|---|
| label of x1 ® a | label of y1→b |
| label of x2→b | label of y2→a |
| label of x3→c | label of y3→g |
| label of x4→d | label of y4→d |
| label of x5→e | label of y5→i |
| label of x6→f | label of y6→f |
| label of x7→g | |
| label of x8→h | |

TABLE 2

| sample vector $\vec{Z}$ | evaluation function input vector $\vec{Y}$ |
|---|---|
| value of z1→x2 | label of y1→b |
| value of z2→x1 | label of y2→a |
| value of z3→x7 | label of y3→g |
| value of z4→x4 | label of y4→d |
| value of z5→0 or sample mean of label i | label of y5→i |
| value of z6→x6 | label of y6→f |

Here, the order of sample vectors is changed in accordance with the labels of input vectors of the evaluation function so that the order of variables is aligned and the relation with labels of data becomes the same, variables for which sample vectors are excessive are omitted, and for a label missing among the sample vectors, an appropriate variable is allocated and added. Here, the allocated value may be 0, or a mean value of elements of the sample group used when the evaluation function was formed. At this time, labels may be separated based on evaluation results considering label co-occurrence, or those of which effect of co-occurrence has inverse correlation, positive correlation, no correlation or those that must not have any correlation, and the labels may be combined considering the relation of labels to each other, or correlation between labels may be evaluated using the present invention.

Then, a vector after reconfiguring the elements of $$\vec{X} \quad \text{[Expression 26]}$$

is given as $$\vec{Z} \quad \text{[Expression 27]}$$

that includes $\{z1, z2, z3, z4, z5, z6\}$.

When such conversion is performed, x3 and x8, which are excessive, are removed from the items, and 0 or a mean value of i label as the corresponding element in the samples when the evaluation function was prepared, labeled i on the side of evaluation function, is substituted for z5, whereby evaluation becomes possible even when elements of vectors to be evaluated differ from those of the evaluation function.

Further, at this time, as to the order of evaluation of vectors on the evaluation function side, labels and element values may be sorted in the order starting from the largest maximum eigen vector, and sample vectors may also be sorted accordingly, and by introducing similar reference, distance or similarity may be evaluated. Further, when 0s, extremely small values or values close to the mean frequently appear as the input vectors, element values of such label or ID portions having the extremely small values or values close to the mean are regarded as 0 and the dimension is reduced using Gaussian elimination, with respect to the covariance matrix based on the variance and mean of the samples used for forming the evaluation function, and the evaluation function itself may also be reduced and re-configured, or when an item of the input vector is 0 or a mean value, the process for calculating distance corresponding to the item may be omitted, whereby operation efficiency is improved and operation speed per unit time may be increased.

Similarly, also in a vector-to-vector situation, a method in which modification is made also on the side of vectors to be evaluated is used, where the input vector is changed from $$\vec{X} \quad \text{[Expression 28]}$$

to $$\vec{Z} \quad \text{[Expression 29]}$$

and the vector to be evaluated is changed from $$\vec{Y} \quad \text{[Expression 30]}$$

to $$\vec{W} \text{[Expression 31]}$$

and in this manner the elements may be reconfigured. Here, though 0 is substituted for the vector element in the example below, the value of this element may be a mean of the samples of respective element values of the population to which the vector on the side containing the element belongs. Such a change of elements based on matching of labels or IDS as identifiers may be used not only for vector analysis but also for multi-dimensional evaluation information such as matrix analysis or tensor analysis. Further, based on the vector configuration with the elements changed, eigen value or eigen vector may be obtained, various transition matrixes such as covariance matrix, probability transition matrix, steady transition matrix, state transition matrix, or arbitrary matrix such as co-occurrence matrix or transition probability matrix of co-occurrence matrix or the like may be formed, or an arbitrary evaluation function may be reconfigured.

TABLE 3

| sample vector $\vec{X}$ | vector to be evaluated $\vec{Y}$ |
|---|---|
| label of x1→a | label of y1→b |
| label of x2→b | label of y2→a |
| label of x3→c | label of y3→g |
| label of x4→d | label of y4→d |
| label of x5→e | label of y5→i |
| label of x6→f | label of y6→f |
| label of x7→g | |
| label of x8→h | |

TABLE 4

| label | sample vector $\vec{Z}$ | vector to be evaluated $\vec{W}$ |
|---|---|---|
| a | value of z1→x1 | value of w1→y2 |
| b | value of z2→x2 | value of w2→y1 |
| c | value of z3→x3 | value of w3→0 |
| d | value of z4→x4 | value of w4→y4 |
| e | value of z5→x5 | value of w5→0 |
| f | value of z6→x6 | value of w6→y6 |
| g | value of z7→y7 | value of w7→y3 |
| h | value of z8→y8 | value of w8→0 |
| i | value of z9→0 | value of w9→y5 |

By aligning evaluation items and using an arbitrary dummy data to an empty item where there is no corresponding element or by arbitrarily adding or omitting on the evaluating side and evaluated side, matching using common element labels becomes possible. Consequently, it becomes possible to evaluate distance or correlation between pieces of information of different elements of evaluation, of which evaluation has been impossible. Here, a method is readily conceived in which the evaluation distance in accordance with the present invention is used as an element, and associated with an element label of an evaluation function or an element label of a sample, whereby the sample may be re-evaluated or the function may be re-evaluated to realize hierarchical structure, with the distance evaluated by the function. Further, rather than reconfiguring the input vector of the evaluation function as in the present embodiment, the order or items of covariance matrix to be used for the evaluation function may be reconfigured, to attain similar effects. As to the distance evaluation, assume that there are an evaluation function X associated with sample A and an evaluation function Y associated with sample B, and distance evaluation of A using evaluation function Y and distance evaluation of B using evaluation function X are performed. Here, if it is close for sample A and function Y and it is far for sample B and function X, the destination where the sample belongs or the information processing means may be changed and learning may be performed again.

Such vector reconfiguration may be realized by forming a program using a combination of various algorithms used for label processing such as addition/deletion/change/exchange of an index of buffering, cue or conventional sort algorithm, and label matching process using DP, HMM or regular expression. Specifically, a label is designated as an identifier of each variable input to the function. Each variable of the input sample is labeled. Whether labels match or not is evaluated, and, if they do not match, a dummy data is inserted to the sample side if the label exists on the function and not on the sample. As the dummy data, a mean value of the item or 0, or an arbitrary multiple of standard deviation may be used. If the label is on the sample and not on the function, the variable on the sample side itself may be removed. Distance is evaluated with the evaluation function thus prepared, and the degree of assignment relevancy is output based on the mean, variance and standard deviation thereof. In this manner, the procedure is executed.

Further, the number of evaluation dimensions of the evaluation function may be dynamically controlled such that high-speed classification process is once performed using an evaluation function of small number of evaluation dimensions on the samples, and thereafter, thus classified samples may be again subjected to finer classification using an evaluation function with higher number of evaluation dimensions, so that rough result can be expected beforehand and how much the expected result and the result of fine classification match is again evaluated, and in this manner, a flexible approach for classification may be possible. Further, the result of re-evaluation may be used as features, for the feature vector of the present invention.

An arbitrary number of eigen values and/or arbitrary number of eigen vectors obtained based on such operations may be used as features, or such eigen values or eigen vectors may be used as evaluation functions in a hierarchy of an arbitrary number. Further, the number of evaluation dimensions of each evaluation function may be used as features. Here, by way of example, the distance is normalized, thereafter, the mean is regarded as one-half the maximum number of dimensions, the dimension may be set to 98 if probability of appearance is 98%, 50 if probability of appearance is 50%, or 5 if probability of appearance is 5%, or in reverse manner, the dimension may be set to 2 if probability of appearance is 98%, or 25 if probability of appearance is 75%, assuming that the number of dimensions as a whole is 100, and thus, distance or probability of appearance may be used as a variable of evaluation function, establishing correlation with the probability of assignment based on the probability density function.

Further, a function evaluating truth and a function evaluating false may be prepared for the evaluation function used for evaluating distance, and evaluation may be made such that if it is close to truth and far from false, it is true, if it is close to false and far from truth, it is false, if both are close, determination is impossible but relativeness is high, and if both are far, determination is impossible but relativeness is low.

When information in a multi-order, multi-dimensional information space of vectors, matrixes or tensors is evaluated, the distance evaluation using an evaluation function such as used in the present invention may be considered to be a method of evaluation using a multi-dimensional polynominal for evaluating approximation of ultraspheres. Next, it is known that there is no set of integers x, y and z that satisfy $x^n+y^n=z^n$, where n is an integer larger than 2, that is, Fermat's theorem, and that there is no algebraic solution for a 5-th or higher degree equation according to Ruffini, Abel and Galoi, and hence such solutions must be obtained using a matrix or the like. Further, it is also well known that a matrix can be converted to a wave function.

From the foregoing, Mahalanobis distance evaluation may be regarded as the following multi-dimensional polynominal.

$$D^2 = \left(\sum_{i=0}^{n}(\overline{X}-x_i)\cdot V_{i0}\right)_0^2 + \left(\sum_{i=0}^{n}(\overline{X}-x_i)\cdot V_{i1}\right)_1^2 + \ldots +$$ [Expression 32]

-continued
$$\left(\sum_{i=0}^{n}(\overline{X}-x_i)\cdot V_{i(n-1)}\right)_{n-1}^2 + \left(\sum_{i=0}^{n}(\overline{X}-x_i)\cdot V_{in}\right)_n^2 (n>4)$$

Considering that the covariance matrix V based on eigen vector is divided by a root of an eigen value, the distance D is calculated based on a polynominal structure, and that difference of a sample from the mean of each element is multiplied by the covariance matrix V based on the eigen vector, it is expected that in an equation used for multi-dimensional distance calculation or Bayesian discrimination equation, the result of operation value cannot be represented by finite digits where n>4 or dependent on a constant or prior probability based on the eigen value as a correction term, and that any of the various element variables would not have finite digits, considering that a recursive or hierarchical evaluation is performed. Further, as can be understood from sampling theorem, information can be reproduced up to only a half of the acquired sample accuracy, and in order to quantify information, it is necessary to establish the resolution and scope of the space, and hence, it is expected that perfect information cannot be obtained unless a limit is set in accordance with the intended target. From the foregoing, it is highly possible that continuous representation or transmission of information with finite digits becomes difficult in a multi-dimensional space. If a solution of such a multi-dimensional polynominal or a value of an element variable cannot be represented in finite digits, it becomes impossible to obtain a stable quantization reference in the multi-dimensional space, so that the result of operation always involves an error, of which accumulation with number of times of operations or with time may results in chaos.

Considering these points, in a multi-dimensional information space that varies time sequentially such as the nature, objective quantification is impossible without at least specifying four axes, including the scope of time axis (amount of variation) and the scope of space axis, re-calculation based on quantification must be performed in time-sequential manner, and hence, in order to quantitatively perform arithmetic prediction using the multi-dimensional polynominal such as described above, only possible approach is to obtain a predicted solution in probabilistic manner using the method of the invention or the like or to obtain a predicted solution by a side-on evaluation method using an equation with the space reduced to a lower dimension.

It is readily understood that the embodiments disclosed here are available in relation with arbitrary published patents, literature or technique and may be improved in accordance with the characteristics thereof.

Although the present invention has been described and illustrated in detail, it is clearly understood that the same is by way of illustration and example only and is not to be taken by way of limitation, the spirit and scope of the present invention being limited only by the terms of the appended claims.

The invention claimed is:

1. An information classifying device, comprising:
   distance calculating means for calculating distance information between each of an arbitrary number of pieces of sample information and center of gravity of each of an arbitrary number of populations including said pieces of sample information, using a distance evaluation function;
   statistical information calculating means for calculating statistical information using mean of sample distances and variance of sample distances with the mean of sample distances being the center, based on each group of distance information constituted by said distance information calculated by said distance calculating means, associated with each said sample information belonging to each said population;

degree of assignment relevancy evaluating means for evaluating degree of assignment relevancy, by calculating distance between the center of gravity of each said population and sample information as an object of classification using said distance calculating means, normalizing said distance using said statistical information calculated by said statistical information calculating means on said calculated distance and performing a statistical test;

assignment destination determining means for determining to which population said piece of information as the object of classification is to be assigned, according to the degree of assignment relevancy evaluated by said degree of assignment relevancy evaluating means; and sample information classifying means for assigning and classifying said piece of sample information as the object of classification to the population determined by said assignment destination determining means.

2. The information classifying device according to claim 1, wherein
said statistical information is statistical information formed by further adding standard deviation of sample distance based on each group of said distance information belonging to each said population; and
said assignment relevancy evaluating means evaluates degree of assignment relevancy of said sample information as the object of classification to each said population, dependent on a probability of assignment to each population, obtained by calculating distance between the center of gravity of each said population and said sample information as the object of classification using said distance evaluation function by said distance calculating means, and normalizing the distance to each said sample information as the object of classification with said standard deviation using said calculated distance and said statistical information calculated by said statistical information calculating means.

3. The information classifying device according to claim 1, wherein
said distance calculating means further includes distance evaluation function reconfiguring means for reconfiguring, after said sample information classifying means forms updated populations having sample information groups updated based on said sample information as the object of classification, the distance evaluation function to be used by said distance calculating means, in accordance with classified group of sample information for each updated population thus formed; and
said distance calculating means further calculates a group of distance information between the sample information as the object of classification belonging to each said updated population and the center of gravity of the updated population, using the distance evaluation function reconfigured by said distance evaluation function reconfiguring means.

4. An information recognizing device, comprising:
the information classifying device according to claim 3; and
recognizing means for performing a process of recognizing identification information corresponding to a feature extracted from natural information using said distance evaluation function reconfigured by said distance evaluation function reconfiguring means.

5. An information searching device, comprising:
the information classifying device according to claim 3;
recognizing means for performing a process of recognizing identification information corresponding to a feature extracted from natural information using said distance evaluation function reconfigured by said distance evaluation function reconfiguring means; and
searching means for performing a search, using result of recognition by said recognizing means.

6. The information classifying device according to claim 1, wherein
said assignment destination determining means includes population generating means for generating a new population when degree of assignment relevancy to every population is out of a prescribed range, and determines that said piece of sample information as the object of classification is assigned to the generated.

7. The information classifying device according to claim 6, wherein
said degree of assignment relevancy is deviation from the mean of distance information group for the population; and
said prescribed degree is in a range in which said deviation is from said mean to a prescribed multiple of standard deviation.

8. The information classifying device according to claim 6, further comprising:
population removing means for removing a population that does not contain at least a prescribed number of pieces of sample information, and for assigning pieces of sample information that belonged to the removed population to another population.

9. The information classifying device according to claim 1, wherein
said assignment destination determining means determines that said piece of sample information as the object of classification is assigned to a population to which degree of assignment relevancy evaluated by said degree of assignment relevancy evaluating means is the highest.

10. The information classifying device according to claim 1, wherein
said distance calculating means calculates said distance information based on covariance structure analysis.

11. The information classifying device according to claim 1, wherein
said distance calculating means calculates said distance information based on an eigenvalue and an eigenvector.

12. The information classifying device according to claim 1, wherein
said distance calculating means calculates Mahalanobis distance as said distance information.

13. The information classifying device according to claim 1, wherein
said distance calculating means calculates distance in accordance with Bayesian discrimination function as said distance information.

14. The information classifying device according to claim 1, wherein
said distance calculating means includes distance normalizing means for normalizing the calculated distance information.

15. The information classifying device according to claim 1, wherein
said piece of sample information as the object of classification is an arbitrary vector information, matrix information or tensor information with an identifier allotted beforehand to each element;

said distance evaluation function is a function having the vector information, matrix information or tensor information of a prescribed element configuration with an identifier allotted beforehand to each element; and said distance calculating means calculates said distance information by reconfiguring each element of said arbitrary vector information, matrix information or tensor information such that the identifier of each element of said arbitrary vector information, matrix information or tensor information becomes the same as the identifier of the element of said prescribed element configuration, and inputting to said distance evaluation function.

16. An information classification method executed by a computer, comprising the steps of:

calculating, by a distance information calculating device configured within the computer, distance information between each of an arbitrary number of pieces of sample information and center of gravity of each of an arbitrary number of populations including said pieces of sample information, using a distance evaluation function;

calculating, by a statistical information calculating device configured within the computer, statistical information using mean of sample distances and variance of sample distances with the mean of sample distances being the center, based on each group of distance information constituted by said calculated distance information, associated with each said sample information belonging to each said population;

evaluating, by a degree of assignment relevancy evaluating unit configured within the computer, degree of assignment relevancy by calculating distance between the center of gravity of each said population and sample information as an object of classification and normalizing said distance using said calculated statistical information on said calculated distance and performing a statistical test;

determining, by an assignment destination determining unit configured within the computer, to which population said piece of information as the object of classification is to be assigned, in accordance with the evaluated degree of assignment relevancy; and assigning and classifying, by a sample information classifying unit configured within the computer, said piece of sample information as the object of classification to the determined population.

17. The information classifying method according to claim 16, wherein said piece of sample information as the object of classification is an arbitrary vector information, matrix information or tensor information with an identifier allotted beforehand to each element;

said distance evaluation function is a function having the vector information, matrix information or tensor information of a prescribed element configuration with an identifier allotted beforehand to each element; and in said step of calculating said distance information, said distance information is calculated by reconfiguring each element of said arbitrary vector information, matrix information or tensor information such that the identifier of each element of said arbitrary vector information, matrix information or tensor information becomes the same as the identifier of the element of said prescribed element configuration, and inputting to said distance evaluation function.

18. A computer-readable medium, storing a set of instructions, executed by a processor, to perform an information classifying method, comprising:

calculating distance information between each of an arbitrary number of pieces of sample information and center of gravity of each of an arbitrary number of populations including said pieces of sample information, using a distance evaluation function;

calculating statistical information using mean of sample distances and variance of sample distances with the mean of sample distances being the center, based on each group of distance information constituted by said calculated distance information, associated with each said sample information belonging to each said population;

evaluating degree of assignment relevancy by calculating distance between the center of gravity of each said population and sample information as an object of classification and normalizing said distance using said calculated statistical information on said calculated distance and performing a statistical test;

determining to which population said piece of information as the object of classification is to be assigned, in accordance with the evaluated degree of assignment relevancy; and assigning and classifying said piece of sample information as the object of classification to the determined population.

19. The computer-readable medium according to claim 18, wherein said piece of sample information as the object of classification is an arbitrary vector information, matrix information or tensor information with an identifier allotted beforehand to each element;

said distance evaluation function is a function having the vector information, matrix information or tensor information of a prescribed element configuration with an identifier allotted beforehand to each element; and in said step of calculating said distance information, said distance information is calculated by reconfiguring each element of said arbitrary vector information, matrix information or tensor information such that the identifier of each element of said arbitrary vector information, matrix information or tensor information becomes the same as the identifier of the element of said prescribed element configuration, and inputting to said distance evaluation function.

20. An information classifying system, comprising:

an information classifying device, and an information terminal connected to said information classifying device through a communication line; wherein said information classifying device includes population receiving means for receiving an arbitrary number of populations including pieces of sample information, from said information terminal, distance calculating means for calculating distance information between each of an arbitrary number of pieces of sample information included in said populations received by said population receiving means and center of gravity of each of the arbitrary number of populations, using a distance evaluation function, statistical information calculating means for calculating statistical information using mean of sample distances and variance of sample distances with the mean of sample distances being the center, based on each group of distance information constituted by said distance information calculated by said distance calculating means, associated with each said sample information belonging to each said population, degree of assignment relevancy evaluating means for evaluating degree of assignment relevancy, by calculating distance between the center of gravity of each said population and sample information as an object of classification using said distance calculating means, and normalizing said distance using said statistical information calculated by said statistical information calculating means on said calculated distance and performing a statistical test, assignment destination determining means for determining to which population said piece of information as the object of classification is to be assigned, according to the degree of assignment relevancy determined by said degree of assignment relevancy determining means, sample information classifying means for assigning and classifying said piece of sample information as the object of classification to the population determined by said assignment destination determining means, and classified population passing means for passing a classified population to which said piece of sample information as the object of classification has been assigned and classified by said sample information classifying means, to said information terminal; and said information terminal includes population passing means for passing said arbitrary number of populations to said information classifying device, and classified population receiving means for receiving said classified population from said information classifying device.

21. An information classifying system, comprising:

an information classifying device, and an information terminal connected to said information classifying device through a communication line; wherein said information classifying device includes sample information receiving means for receiving a piece of sample information as an object of classification from said information terminal, distance calculating means for calculating distance information between each of an arbitrary number of pieces of sample information including sample information as an object of classification received by said sample information receiving means and center of gravity of each of the arbitrary number of populations including said sample information, using a distance evaluation function, statistical information calculating means for calculating statistical information using mean of sample distances and variance of sample distances with the mean of sample distances being the center, based on each group of distance information constituted by said distance information calculated by said distance calculating means, associated with each said sample information belonging to each said population, degree of assignment relevancy evaluating means for evaluating degree of assignment relevancy, by calculating distance between the center of gravity of each said population and sample information as an object of classification using said distance calculating means, and normalizing said distance using said statistical information calculated by said statistical information calculating means on said calculated distance and performing a statistical test, assignment destination determining means for determining to which population said piece of information as the object of classification is to be assigned, according to the degree of assignment relevancy determined by said degree of assignment relevancy determining means, and population identifying information passing means for passing population identifying information identifying the population determined by said assignment destination determining means to said information terminal; and said information terminal includes sample information passing means for passing said piece of sample information as the object of classification to said information classifying device, and population identifying information receiving means for receiving said population identifying information from said information classifying device.

22. The information classifying system according to claim 20 or 21, wherein said piece of sample information as the object of classification is an arbitrary vector information, matrix information or tensor information with an identifier allotted beforehand to each element;

said distance evaluation function is a function having the vector information, matrix information or tensor information of a prescribed element configuration with an identifier allotted beforehand to each element; and said distance calculating means calculates said distance information by reconfiguring each element of said arbitrary vector information, matrix information or tensor information such that the identifier of each element of said arbitrary vector information, matrix information or tensor information becomes the same as the identifier of the element of said prescribed element configuration, and inputting to said distance evaluation function.

23. An information providing service, using an information classifying system including an information classifying device, and an information terminal connected to said information classifying device through a communication line; wherein said information classifying device includes sample information receiving means for receiving a piece of sample information as an object of classification from said information terminal, distance calculating means for calculating distance information between each of an arbitrary number of pieces of sample information including sample information as an object of classification received by said sample information receiving means and center of gravity of each of the arbitrary number of populations including said sample information, using a distance evaluation function, statistical information calculating means for calculating statistical information, using mean of sample distances and variance of sample distances with the mean of sample distances being the center, based on each group of distance information constituted by said distance information calculated by said distance calculating means, associated with each said sample information belonging to each said population, degree of assignment relevancy evaluating means for evaluating degree of assignment relevancy, by calculating distance between the center of gravity of each said population and sample information as an object of classification using said distance calculating means, and normalizing said distance using said statistical information calculated by said statistical information calculating means on said calculated distance and performing a statistical test, assignment destination determining means for determining to which population said piece of information as the object of classification is to be assigned, according to the degree of assignment relevancy determined by said degree of assignment relevancy determining means, and population identifying information passing means for passing population identifying information identifying the population determined by said assignment destination determining means to said information terminal; and said information terminal includes sample information passing means for passing said piece of sample information as the object of classification to said information classifying device, and population identifying information receiving means for receiving said population identifying information from said information classifying device.

24. The information providing service using the information classifying system according to claim 23, wherein said piece of sample information as the object of classification is an arbitrary vector information, matrix information or tensor information with an identifier allotted beforehand to each element;

said distance evaluation function is a function having the vector information, matrix information or tensor information of a prescribed element configuration with an identifier allotted beforehand to each element; and said distance calculating means calculates said distance information by reconfiguring each element of said arbitrary vector information, matrix information or tensor information such that the identifier of each element of said arbitrary vector information, matrix information or tensor information becomes the same as the identifier of the element of said prescribed element configuration, and inputting to said distance evaluation function.

25. An information classifying system, comprising:

an information classifying device, and an information terminal connected to said information classifying device through a communication line; wherein said information classifying device includes population receiving unit configured to receive an arbitrary number of populations including pieces of sample information, from said information terminal, distance calculating unit configured to calculate distance information between each of an arbitrary number of pieces of sample information included in said populations received by said population receiving unit and center of gravity of each of the arbitrary number of populations, using a distance evaluation function, statistical information calculating unit configured to calculate statistical information using mean of sample distances and variance of sample distances with the mean of sample distances being the center, based on each group of distance information constituted by said distance information calculated by said distance calculating unit, associated with each said sample information belonging to each said population, degree of assignment relevancy evaluating unit configured to evaluate degree of assignment relevancy, by calculating distance between the center of gravity of each said population and sample information as an object of classification using said distance calculating unit, and normalizing said distance using said statistical information calculated by said statistical information calculating unit on said calculated distance and performing a statistical test, assignment destination determining unit configured to determine to which population said piece of information as the object of classification is to be assigned, according to the degree of assignment relevancy determined by said degree of assignment relevancy determining unit, sample information classifying unit configured to assign and classify said piece of sample information as the object of classification to the population determined by said assignment destination determining unit, and classified population passing unit configured to pass a classified population to which said piece of sample information as the object of classification has been assigned and classified by said sample information classifying unit to said information terminal; and said information terminal includes population passing unit configured to pass said arbitrary number of populations to said information classifying device, and classified population receiving unit configured to receive said classified population from said information classifying device.

26. The information classifying system according to claim 25, wherein said piece of sample information as the object of classification is an arbitrary vector information, matrix information or tensor information with an identifier allotted beforehand to each element;

said distance evaluation function is a function having the vector information, matrix information or tensor information of a prescribed element configuration with an identifier allotted beforehand to each element; and said distance calculating unit is configured to calculate said distance information by reconfiguring each element of said arbitrary vector information, matrix information or tensor information such that the identifier of each element of said arbitrary vector information, matrix information or tensor information becomes the same as the identifier of the element of said prescribed element configuration, and inputting to said distance evaluation function.

27. An information classifying system comprising:

an information classifying device, and an information terminal connected to said information classifying device through a communication line; wherein said information classifying device includes sample information receiving unit for receiving a piece of sample information as an object of classification from said information terminal, distance calculating unit for calculating distance information between each of an arbitrary number of pieces of sample information including sample information as an object of classification received by said sample information receiving unit and center of gravity of each of the arbitrary number of populations including said sample information, using a distance evaluation function, statistical information calculating unit for calculating statistical information, using mean of sample distances and variance of sample distances with the mean of sample distances being the center, based on each group of distance information constituted by said distance information calculated by said distance calculating unit, associated with each said sample information belonging to each said population, degree of assignment relevancy evaluating unit for evaluating degree of assignment relevancy, by calculating distance between the center of gravity of each said population and sample information as an object of classification using said distance calculating unit, and normalizing said distance using said statistical information calculated by said statistical information calculating unit on said calculated distance and performing a statistical test, assignment destination determining unit for determining to which population said piece of information as the object of classification is to be assigned, according to the degree of assignment relevancy determined by said degree of assignment relevancy determining unit, and population identifying information passing unit for passing population identifying information identifying the population determined by said assignment destination determining unit to said information terminal; and said information terminal includes sample information passing unit for passing said piece of sample information as the object of classification to said information classifying device, and population identifying information receiving unit for receiving said population identifying information from said information classifying device.

28. The information classifying system according to claim 27, wherein said piece of sample information as the object of classification is an arbitrary vector information, matrix information or tensor information with an identifier allotted beforehand to each element;

said distance evaluation function is a function having the vector information, matrix information or tensor information of a prescribed element configuration with an identifier allotted beforehand to each element; and said distance calculating unit calculates said distance information by reconfiguring each element of said arbitrary vector information, matrix information or tensor information such that the identifier of each element of said arbitrary vector information, matrix information or tensor information becomes the same as the identifier of the element of said prescribed element configuration, and inputting to said distance evaluation function.

* * * * *